US009234846B2

(12) United States Patent
Kalkbrenner et al.

(10) Patent No.: US 9,234,846 B2
(45) Date of Patent: Jan. 12, 2016

(54) HIGH-RESOLUTION MICROSCOPE AND METHOD FOR DETERMINING THE TWO- OR THREE-DIMENSIONAL POSITIONS OF OBJECTS

(75) Inventors: Thomas Kalkbrenner, Jena (DE); Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 551 days.

(21) Appl. No.: 13/518,064

(22) PCT Filed: Dec. 14, 2010

(86) PCT No.: PCT/EP2010/007595
§ 371 (c)(1),
(2), (4) Date: Sep. 24, 2012

(87) PCT Pub. No.: WO2011/085766
PCT Pub. Date: Jul. 21, 2011

(65) Prior Publication Data
US 2013/0010098 A1 Jan. 10, 2013

(30) Foreign Application Priority Data
Dec. 22, 2009 (DE) .......... 10 2009 060 793

(51) Int. Cl.
G01N 21/64 (2006.01)
G02B 27/58 (2006.01)
G02B 21/36 (2006.01)
G02B 21/16 (2006.01)

(52) U.S. Cl.
CPC ........ *G01N 21/6458* (2013.01); *G01N 21/6428* (2013.01); *G02B 21/16* (2013.01); *G02B 21/361* (2013.01); *G02B 21/367* (2013.01); *G02B 27/58* (2013.01)

(58) Field of Classification Search
CPC .......... G01N 21/6428; G01N 21/6458; G02B 27/58; G02B 21/361; G02B 21/367; G02B 21/16
See application file for complete search history.

(56) References Cited

U.S. PATENT DOCUMENTS

| 5,866,911 | A | 2/1999 | Baer |
| 5,867,604 | A * | 2/1999 | Ben-Levy et al. ............ 382/254 |
| 6,064,472 | A * | 5/2000 | Drewling ..................... 356/28.5 |
| 6,388,788 | B1 * | 5/2002 | Harris et al. ................ 359/196.1 |
| 6,633,432 | B2 * | 10/2003 | Iketaki .......................... 359/386 |
| 8,217,992 | B2 * | 7/2012 | Bewersdorf et al. ............ 348/47 |
| 2009/0134342 | A1 * | 5/2009 | Hell et al. .................. 250/459.1 |
| 2009/0237501 | A1 * | 9/2009 | Lemmer et al. ................. 348/79 |
| 2010/0330578 | A1 * | 12/2010 | Duhr et al. ........................ 435/6 |
| 2011/0043619 | A1 * | 2/2011 | Wolleschensky ............... 348/79 |
| 2011/0275932 | A1 * | 11/2011 | Leblond et al. ............... 600/425 |

FOREIGN PATENT DOCUMENTS

| DE | 28 34 204 A1 | 3/1980 |
| DE | 4416558 A1 | 8/1995 |
| DE | 19829981 A1 | 1/2000 |
| DE | 19835072 A1 | 2/2000 |
| DE | 19930532 A1 | 1/2001 |
| DE | 10259443 A1 | 7/2004 |
| DE | 10325460 A1 | 11/2004 |
| EP | 1157297 A1 | 11/2001 |
| WO | WO 2006/127692 A2 | 11/2006 |
| WO | WO 2007/009812 A1 | 1/2007 |

OTHER PUBLICATIONS

Huang, Bo, et al.; "Three-Dimensional Super-Resolution Imaging by Stochastic Optical Reconstruction Microscopy"; Science Feb. 8, 2008; 319:810-813.
Hess, Samuel T., et al.; "Ultra-High Resolution Imaging by Fluorescence Photoactivation Localization Microscopy"; Biophysical Journal, Dec. 2006; 91:4258-4272.
Vaziri, Alipasha, et al.; "Multilayer three-dimensional super resolution imaging of thick biological samples"; PNAS Dec. 23, 2008; 105(51):20221-20226.
Toprak, Erdal, et al.; "Three-Dimensional Particle Tracking via Bifocal Imaging"; Nano Letters 2007; 7(7):2043-2045.
Ram, et al.; "High Accuracy 3D Quantum Dot Tracking w/Multifocal Plane Microscopy for the Study of Fast Intracellular Dynamics in Live Cells"; Biophysical Journal,956025-6043.
Yajima, Junichiro, et al.; "A torque component present in mitotic kinesin Eg5 revealed by three-dimensional tracking"; Nature Structural & Molecular Biology; 15(10):1119-1121.
Eric Betzig, et al., "Imaging Intracellular Fluorescent Proteins at Nanometer Resolution", Science (2006), 313:1642-1645.

Hess, et al., "Dynamic clustered distribution of hemagglutinin sresolved at 40 nm in living cell membranes discriminates between raft theories", PNAS (2007);104(44):17370-17375.

Hari Shroff, et al., "Dual-color superresolution imaging of genetically expressed probes within individual adhesion complexes", PNAS (2007), 104(51):20308-20313.

Rust, Michael J., et al.; "Sub-diffraction-limit imaging by stochastic optical reconstruction microscopy (STORM)"; Nature Methods (2006), 3(10):793-796.

Alexander Egner, et al., "Fluorescence Nanoscopy in Whole Cells by Asynchronous Localization of Photoswitching Emitters", Biophysical Journal (2007), 93:3285-3290.

Juette, Manuel F., et al.; "Three-dimensional sub-100 nm resolution fluorescence microscopy of thick samples"; Nature Methods (2008); 5(6):527-529.

Gurskaya, Nadya G., et al., "Engineering of a monomeric green-to-red photoactivatable fluorescent protein induced by blue light"; Nature Biotechnology 2006, 24(4):461-465.

Marriott, Gerard, et al.; "Optical lock-in detection imaging microscopy for contrast-enhanced imaging in living cells"; PNAS 2008, 105(46):17789-17794.

Ivanchenko, Sergey, et al.; "Two-Photon Excitation and Photoconversion of EosFP in Dual-Color 4Pi Confocal Microscopy"; Biophysical Journal 2007, 92:4451-4457.

Oron, Dan, et al.; "Scanningless depth-resolved microscopy"; Optics Express 2005, 13(5):1468-1476.

Folling, Jonas, et al.; "Fluorescence Nanoscopy with Optical Sectioning by Two-Photon Induced Molecular Switching using Continuous-Wave Lasers"; ChemPhysChem 2008, 9:321-326.

Pawley, James B.; Handbook of Biological Confocal Microscopy (3rd Edition); Springer-Science+Business Media, LLC ©2006,1995,1989; Table of Contents.

Watanabe, Wataru, et al.; "Single-organelle tracking by two-photon conversion"; Optics Express 2007, 15(5):2490-2498.

Schneider, Mark, et al.; "Two-Photon Activation and Excitation Properties of PA-GFP in the 720-920-nm Region"; Biophysical Journal 2005, 89:1346-1352.

* cited by examiner

*Primary Examiner* — Jefferey Harold
*Assistant Examiner* — Sean Haiem

(74) *Attorney, Agent, or Firm* — Duane Morris LLP

(57) ABSTRACT

The invention relates to a high-resolution microscope and to a method for determining the two- or three-dimensional positions of objects. The microscope and method includes the following: (a) The vertical (Z) position of imaged particles or molecules being determined from the orientation and shape thereof by means of an anamorphic lens, preferably a cylindrical lens, in the imaging, (b) the detection beam path being split into at least two partial detection beam paths having different optical path lengths, which are detected at an offset on a detector, (c) activation or switchover being performed by means of a multi-photon excitation process, preferably two-photon excitation. The following are also included: (d) a point-scanning activation or switchover, (e) a line-scanning activation or switchover, (f) the sample is excited and the sample light is detected in the wide-field mode, (g) manually or automatically predetermined sample regions are activated or switched over, (h) the activation or switchover is performed by means of AOTF or SLM or DMD, (i) laser pulses for activating or switching are spectrally split by means of a spectrally splitting element, preferably a grating, (j) an SLM or DMD in the beam path after the grating performs a controlled selection of split laser pulse fractions, (k) the laser wide-field excitation is guided by SLM or DMD, (l) ROIs are selected by SLM or DMD, (m) a multi-photon switching or activation is performed by means of a microlens array, preferably a cylindrical lens array, n) switching and/or excitation is performed by means of a line scanner, and (o) a line detection is performed by means of a spatially resolved sensor, wherein at least two sensor rows, each comprising a plurality of sensors, are illuminated with sample light by means of a slit diaphragm position.

40 Claims, 13 Drawing Sheets

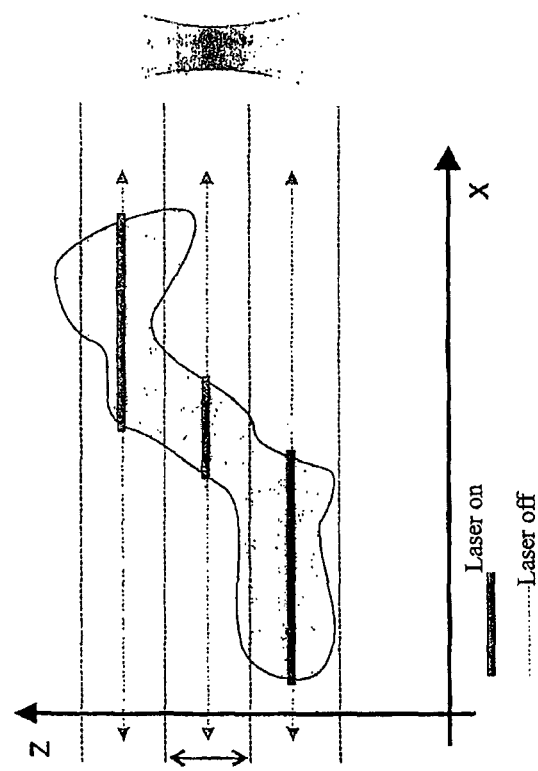
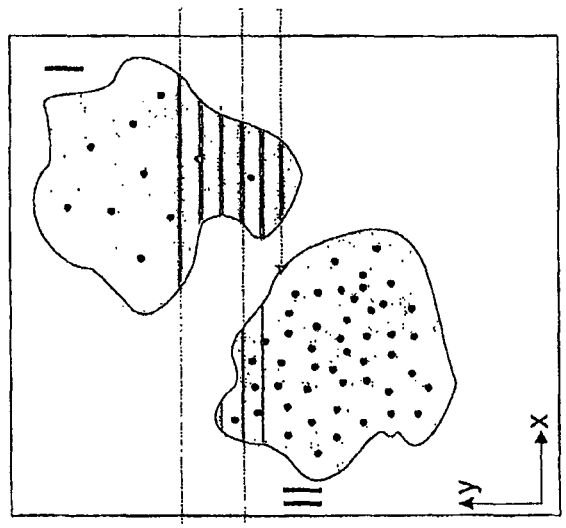
FIG 7a)
FIG 7b)

HIGH-RESOLUTION MICROSCOPE AND METHOD FOR DETERMINING THE TWO- OR THREE-DIMENSIONAL POSITIONS OF OBJECTS

RELATED APPLICATIONS

The present application is a U.S. National Stage application of International PCT Application No. PCT/EP2010/007595 filed on Dec. 14, 2010 which claims priority benefit of German Application No. DE 10 2009 060 793.5 filed on Dec. 22, 2009, the contents of each are incorporated by reference in their entirety.

FIELD OF THE INVENTION

The present invention relates generally to the field of microscopy and more particularly to high-resolution microscopy.

BACKGROUND OF THE INVENTION

In principle, the optical resolution of a light microscope, such as a LSM, is limited with regard to diffraction by the laws of physics. For an optimal resolution within these limits particularly illumination configurations are known, such as 4Pi arrangements or arrangements with fields of stationary waves. Here, the resolution can be considerably improved, particularly in the axial direction, in reference to classic LSM.

Using non-linear depopulation processes, the resolution can be further increased in reference to a diffraction-limited confocal LSM. Such a method is described, e.g., in U.S. Pat. No. 5,866,911. Several approaches are known for the depopulation process, such as described in DE 4416558 C2, U.S. Pat. No. 6,633,432, or DE 10325460 A1.

In recent years, various methods to overcome the diffraction limit have been developed and applied in fluorescence microscopy (PALM structured illumination WO 2006127692; EP 1157297 B1).

A presently particularly advantageous method developed for high-resolution fluorescence microscopy is based on the highly-precise localization of individual molecules. It is known that the localization, thus the determination of the position of an individual fluorescent molecule, is not subject to limits of diffraction.

This localization can occur with highly sensitive cameras in the wide field with a precision up to the nm-range, when sufficient protons of the molecule can be detected. In high-resolution microscopy based on localization an image is composed from the molecule positions obtained in this manner. Here it is critical that at any given time only one subset of molecules of the sample are in a fluorescent state so that on average the "closest neighbor" distance of the active molecules is always greater than the PSF (point spread function) of the microscope. This is achieved by using optically or chemically switched fluorophores: in a tightly marked area of a sample, by way of irradiation of suitable conversion wavelength, stochastic subsets of fluorophores are switched in the examined area into the fluorescent state. Here, the density of the spot is adjusted such that a continuous localization of the positions of the molecules is permitted. This optic switching method is used, for example in PhotoActivated Localization Microscopy (PALM). This fundamental method is described in the literature (listed hereinbelow) in detail, using different variations, see literature items [1-6].

Here, the high-resolution methods (PALM, STORM, D-STORM etc.) primarily differ in the selection of the fluorophores and the type of optic switching process.

However, all methods have in common that the localization of the molecules occurs by an imaging process on a highly sensitive camera (e.g., EMCCD). The quasi-punctual light source (molecule) is here displayed by the point spread function (PSF) of the microscope over several camera pixels. The precise position of the molecule in the x/y-level can now be determined either by fitting the known PSF (Gauss) or by a determination of the focus or by a mixture of both (Gaussian mask) (see the literature, citing different algorithms).

Typical precisions of localization range (depending on the experimental conditions) from 5 to 30 nm; this then also represents approximately the lateral resolution of this method. Practically, this calls on the one hand for molecules not being located too close to each other and on the other hand for an illustration of the examined structures as completely as possible, so that many individual images (typically 10,000-20,000) must be taken of the sample. This leads to a rather extensive imaging period as well as to problems with regard to the adjustment of the switching intensity, particularly when the sample and/or the structures of interest are marked very inhomogeneously: in order to prevent losing any information the switching intensity must always be adjusted to the area of the sample marked most densely.

In general, the above-described method based on localized high resolution is limited to surfaces and/or 2 dimensions, because the localization of the individual colorant molecules are considerably more complex in the third dimension (z-direction). The number of accepting individual molecules for illustrating the structures increases accordingly in the three-dimensional case.

Another problem for the three-dimensional high-resolution display in the depth of a sample lies in the limited penetration depth: as already known from the classical fluorescence microscopy and laser-scanning microscopy, the increasingly dispersed excited radiation in the depth of the sample leads to an increase of the background signals with a simultaneous reduction of the actual wanted signal.

In addition to the undesired photo bleaching of sample sections outside the focused level, it also occurs in the PAL-M method that in the depth of the sample undesired switching of the fluorophores occurs by the activating radiation in the layers not presently measured.

In prior art there is the general need for a high-resolution display of fluorescence in three dimensions with high penetration depth and "sectioning" (thus measuring a layer and here avoiding exciting/bleaching and particularly switching the photo-convertible fluorophores in the layers located above or below) and an increase in recording speed.

SUMMARY OF THE INVENTION

According to the invention, it has been recognized that a three-dimensional microscope with increased resolution can be realized using the synergies of the following advantageous technologies and arrangements in the arrangements and methods described in detail in the following:
High-Resolution Determination of an Axial (Z-) Position of Molecules: Astigmatism/Cylinder Lens ([9])

In this approach a weak cylinder lens is inserted into the detection radiation path, which leads to an astigmatic PSF. Accordingly, the image of the molecule is elliptically distorted when the molecule is located above or below the symmetry point of the PSF. Information can then be extracted concerning the z-position of the molecule from the orientation and extent of said distortion. The anamorphotic optic (cylinder lens) is advantageously used according to the invention for determining the vertical position of the molecule by detecting the form and/or size and realized in a microscope using the following methods and arrangements.

Detection in Two Levels (Biplanar Detection) (Toprak et al., Bewersdorf et al. [7,8])

Here, a 50/50 beam splitter is inserted into the detection radiation path, splitting the image into two partial images (duplicated). These two images are either displayed on two identical cameras or side-by-side on a camera chip. An optic difference of path lengths is introduced into one of the two partial radiation paths such that two object levels develop from the two partial radiation paths, apart from each other in the z-direction, by approximately half to one z-PSF (700 nm). The z-position for molecules located between these two levels can now be determined, e.g., by way of subtraction of the two partial images of the molecule and/or by fitting a three-dimensional PSF or a similar algorithm.

The splitting of the detection radiation path and an off-set detection of the split radiation paths, showing a difference in length, as well as the other methods and applications according to the invention are implemented in a microscope.

Penetration Depth: Multiphoton Microscopy

Prior art of multi-proton microscopy, particularly 2-photon (2P) excitation and its advantages, are used in a targeted fashion for the methods and arrangements according to the invention described in the following.

The 2P Switching of Colorants that can be Converted

The possibility of a 2P excitation applies not only for the typical fluorescence excitation of known colorants but in principle also for the change of status of so-called switchable fluorophores or photo-switches. This represents fluorophores, which by the irradiation of a switching wavelength can be set into a fluorescent or non-fluorescent state, depending on the initial state (cf. PALM, STORM, etc.). Here, the switching wavelength may also be equivalent to the excitation wavelength. Such photo switches are essential for the above-mentioned high-resolution methods.

In various publications, see literature item [10], it was reported that some switchable fluorophores can also be switched with a 2-photon excitation, e.g., the proteins dronpa, eosFP, kaede, kikume, PA-GFP (references 2P switching).

The 2P activation (switching into a state that can be activated) is particularly used in the point scanning mode, but also in the line scanning mode, preferably with wide-field fluorescence excitation and wide-field detection, individually or with other arrangements and methods used according to the invention.

They are particularly beneficial in connection with the marking of pre-determined regions (ROI), which, for example, are detected and marked in a preliminary image, such as certain cells or other interesting biological fields, particularly by:

AOTF control, SLM control, or DMD control of the impingement with switching radiation and/or excitation radiation.

This occurs two-dimensionally and three-dimensionally (in the image stack), also in connection with the other methods and arrangements in a microscope listed according to the invention.

Temporal Focusing of the Switching Radiation

Using the so-called temporal focusing, the depth discrimination, which develops in the point-scanning 2P microscopy by the square intensity dependency of the excitation in combination with strong focusing, a wide-field display can, also be achieved. For this purpose, e.g., in literature item [11] short laser pulses are split spectrally via a grid; this grid is then displayed via the lens of the microscope. This leads to the different spectral components of the pulse assuming different optic paths and only merging back in the focal area in order to here form the original short laser pulse. Here, the highest power of the pulse is only maximal in the focal area, which in the context of the above-mentioned square intensity dependency of the 2P excitation leads to a depth discrimination, but now at a wide field.

This may be connected by SLM or DMD control with the ROI function, as mentioned above.

2P Multi-Spot Imaging with a grid micro-lens array or rotary micro-lens disk, e.g., in literature item [14] and references therein is realized in a microscope with other methods and arrangements listed.

Switching and Excitation Via a Lens Scanner are realized in a microscope with the other methods and arrangements listed.

Contrary to the arrangements and methods described in the following, prior art could not achieve the synergies and advantages according to the invention:

PALM and similar methods yield a two-dimensional high-resolution fluorescent image, but only at the cover-glass boundary under TIRF excitation Using bi-planar or astigmatism charges additionally the z-resolution can be increased; the measuring of thicker samples is particularly problematic such that only layers of a dimension of one PSF can be measured. Layers above or below this can be sequentially measured as an image stack, as is common in microscopy; however, since this represents (laser) wide-range excitation and switching, the layers above and below are also switched and/or bleached as early as during the measuring of the present layer, and thus they cannot be measured or only to a limited extent.

Temporal focusing for switching the fluorophores literature item [12] was demonstrated and a 2P-comparable sectioning was observed. However, this way no real 3D-high resolution can be achieved.

2P switching by a point-scanned cw laser in connection with wide-field detection was demonstrated in item [13]. Here, too, it is sectioned; however, no 3D-resolution is possible.

In all localization-based high resolution methods based on photo-switches presently the intensity of the switching laser per image must be adjusted to the highest marker density inside the observed sample range.

LITERATURE

[1] Betzig et al. Science 313, 1642-1645 (2006)
[2] Hess et al., PNAS 104, 17370-17375 (2007)
[3] Hess et al., Biophys J. 91, 4258-427 (2006)
[4] Schroff et al., PNAS 104, 20308-2031 (2007)
[5] Rust et al., Nat Methods 3, 793-796 (2006)
[6] Egner et al., Biophys J. 93, 3285-3290 (2007)
[7] Toprak et al., Nano Lett. 7, 2043-2045 (2007)
[8] Juette et al., Nature Methods 5, 527 (2008)
[9] Huang et al., Science 319, 810 (2008)
[10] Marriot et al. PNAS Vol. 105, #46, pg 17789, 2008, Ivanchenko et al. Biophys J, vol. 92, pgs 4491-4457, 2007, Watanabe et al., Opt Exp., vol. 15, pg 2490, 2007, Schneider et al. Bio Phys J, vol. 89, pg 1346-1352, 2005
[11] Oron et al, Optics Express 13, 1468 (2005)
[12] Vaziri et al., PNAS 105, 20221 (2008)
[13] Fölling et al., Chem Phys Chem 9, 321, (2008)

[14] Pawley, Handbook of Biological Confocal Microscopy (3rd Edition)
DE 19829981A1: Regions of Interest
DE 19930532A1: SLM
DE10259443 A1: Pulse combination in the sample
DE 19835072A1: DMD
U.S. Pat. No. 5,867,604: Structured illumination The invention further has features of the independent claims.

It is realized in a high-resolution microscope and a method for the two- or three-dimensional determination of the position of objects, particularly individual fluorophores, preferably for the spatially high-resolution fluorescent microscopy of a sample marked with marking molecules, which can be activated or switched by a signal such that only in the activated or switched state they can be excited to emit fluorescent radiation, with the method comprising the following steps:

1) Introducing the signal to the sample such that only a partial amount of the marker molecules present in the sample are activated, with partial sections developing in the sample in which activated marker molecules show a distance from the closest neighboring activated marker molecules greater than or equivalent to a length, which results from a predetermined optic resolution,
2) excitation of the activated molecule to emit fluorescent radiation,
3) detection of a fluorescent radiation with a predetermined optic resolution, and
4) generation of an individual image from the luminescent radiation recorded in step 3), with the geometric locations of the marker molecules emitting the fluorescent radiation being determined with a local resolution enhanced beyond the predetermined optic resolution, with the steps being repeated several times and the multitude of individual images yielded in this manner being combined to an overall image.

The invention further advantageously comprises at least one of the arrangements a) to q) of claim 1.

The invention furthermore comprises advantageously at least one of the processing steps a)-o) of claim 2.

BRIEF DESCRIPTION OF THE DRAWINGS

In the following, the invention is explained in greater detail using the schematic drawings, in which:

FIG. 7(a) shows an adjustment of the switching intensity;

FIG. 7(b) shows a schematic image stack in the x-z cross section;

DESCRIPTION OF THE PREFERRED EMBODIMENTS

Figure 1:
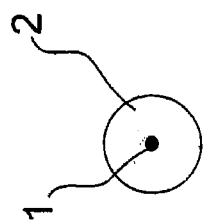
FIG. 1 is a schematic illustration of an activated marker molecule in a volume with limited resolution.

FIG. 1 shows schematically a marker molecule 1, which has been excited for fluorescence. Of course, the detection of fluorescence requires a plurality of excitations, because each excitation yields precisely one fluorescent proton and the detection of radiation requires an integration of many fluorescent protons. The fluorescent radiation emitted by the marker molecules 1 can be detected in a microscope based on physical principles only in a limited optic resolution. Even if the microscope reaches the diffraction limit of the optic resolution the photons of the fluorescent marker molecule 1 are still distributed due to diffraction and thus detected in a diffraction disk 2. The microscope therefore displays an object principally larger than the geometric extension of the marker module 1, drawn in FIG. 1 schematically as a black circle, which is illustrated in FIG. 1 by the diffraction disk 2. The size of the diffraction disk 2 depends on the quality of the microscopy device used and is defined by the half-width of the point spread function of the optic display. Actually, this represents not a two-dimensional object but a diffraction volume, which the fluorescent photons penetrate. In the two-dimensional illustration of FIG. 1 this appears as a disk, though. The term diffraction disk is here used generally for a maximum resolution volume, which the optic used can achieve. It is not mandatory for the optic used to work at the diffraction limit, even if this is preferred.

In order to allow more precisely localizing the marker molecule 1 within the diffraction disk 2 the PALM method is used, already described above in a general fashion. It activates individual marker molecules, with, in this description, generally the term activation relates to the activation of certain luminescent features of the marker molecules, thus both switching on the luminescent excitation as well as a change of the spectrum of luminescence emitted, which is equivalent to switching on certain luminescent features. In the exemplary embodiment described here the activation is caused by optic activation radiation. However, different, non-optic activation mechanisms are also possible.

The activation now occurs such that there are at least some activated molecules, with their focal point not being within the diffraction disk of other activated molecules, i.e. which can still be distinguished, at least within the optic resolution.

Figure 2:
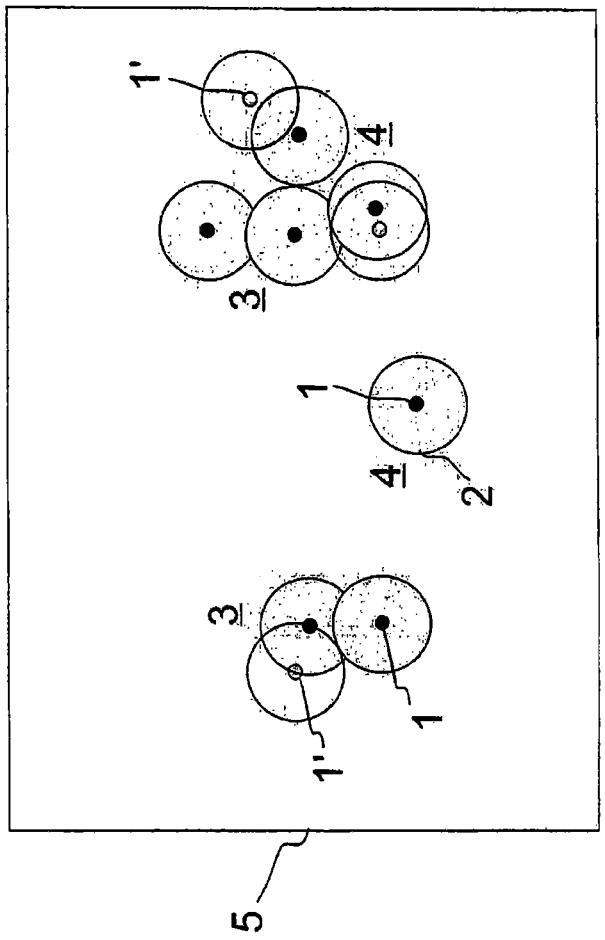
FIG. 2 is a schematic illustration of the image of various activated and non-activated marker molecules on a locally resolving detector.

FIG. 2 shows schematically an exemplary situation on a detector 5, which integrates the protons in a spatially resolving fashion. As discernible, there are areas 3, in which the diffraction disks of adjacent marking molecules overlap. Here, as is discernible in the left area 3 of FIG. 2, only those marker molecules are relevant which have previously been activated. Non-activated marker molecules 1' fail to emit the determined fluorescent radiation, which is detected on the matrix detector 5; thus they are irrelevant.

In the areas 4, e.g., areas 4 located in the center of the matrix detector 5, the marker molecules 1 are located such that their diffraction disk 2 overlaps with none of the diffraction disks of other activated marker molecules 1. The right area of the matrix detector 5 shows that areas 3, in which diffraction disks of activated marker molecules overlap, may indeed be located adjacent to areas 4 in which this is not the case. The right area 4 illustrates additionally that the neighborhood of an activated marker molecule 1 is irrelevant for the detection of a non-activated marker molecule 1', because such a marker molecule 1' emits no fluorescent radiation detected by the matrix detector 5; thus it is not fluorescent.

Figure 3:
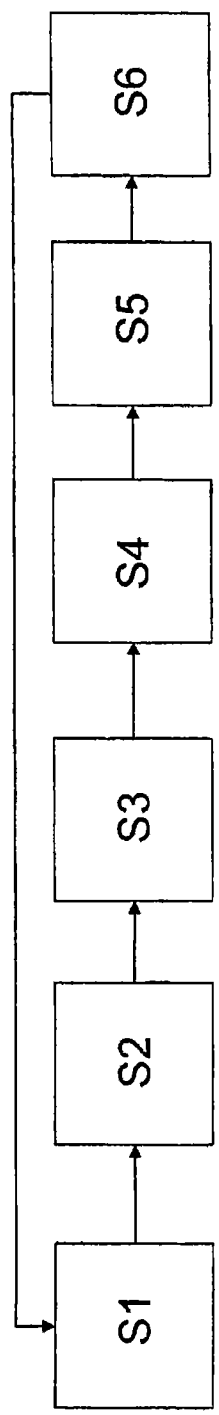
FIG. 3 is a flow chart for the image generation in the PALM method.

In order to record a detailed image beyond the optic resolution predetermined by the device, with the image being a high-resolution image in the sense of this description, now the steps schematically illustrated in FIG. 3 are used.

In a first step S1, using a switching signal, a subset of the marker molecules is activated; they are therefore switched from a first state, in which they cannot be excited to emit the certain fluorescent radiation, into a second state, in which they can be excited to emit the certain fluorescent radiation. Of course, the activation signal can also lead to a selective deactivation, thus in step S1 an inverse process may be used, too. It is essential that after the step S1 only a subset of the marker molecules can be excited to emit certain fluorescent radiation. The activation and/or deactivation (in the following for reasons of simplification only the case of activation is being discussed) occurs independent from the marker molecules used. In a colorant, such as DRONPA, PA-GFP, or reversibly switchable synthetic colorants (such as Alexa/cyan constructs), the activation occurs by optic radiation; the switching signal is therefore a switching radiation.

Figure 4:
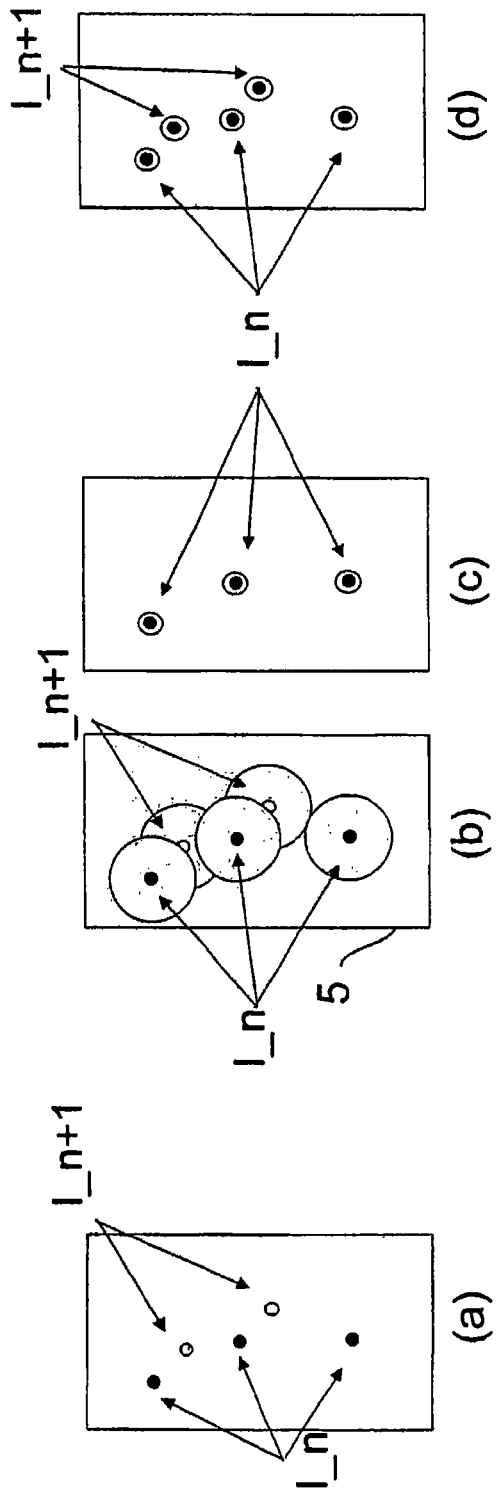
FIG. 4 is explanatory illustrations allocated to the flow chart of FIG. 3 of the marker molecules displayed on the detector of FIG. 2.

FIG. 4, shown under FIG. 3, illustrates in detail the condition after step S1. Only a subset of the marker module $1\_n$ is activated, here. The marker molecule of this subset is represented by a filled black dot. The remaining marker molecules have not been activated in this step. They are marked $1\_n+1$ in detail a of FIG. 4.

Marker molecules, which have been activated, may then be excited in a second step S2 to emit fluorescent radiation. Used as fluorescent colorants are preferably fluorescent proteins, known from prior art, such as PA-GFP or also DRONPA. The activation occurs in such molecules with radiation at a range of approx. 405 nm, the excitation for fluorescent radiation at a wavelength of approx. 488 nm, and the fluorescent radiation is in a range above 490 nm.

In a third step S3 the emitted fluorescent radiation is detected, for example by integration of the recorded fluorescence photons, so that the situations develop on the matrix detector 5 shown in the detail b of FIG. 4 located thereunder. As discernible, the diffraction disks of the activated marker molecules $1\_n$ are not overlapping. The size of the diffraction disks is determined by the optic resolution of the display on the matrix detector 5. Additionally, in the detail b of FIG. 4 (theoretic) diffraction disks of fluorescent molecules are drawn, not included in the non-activated group $1\_n+1$. Due to the fact that these non-activated marker molecules emit no fluorescent radiation no fluorescent radiation located in the (theoretic) diffraction disks can compromise the detection of the fluorescent radiation of the subset $1\_n$ of the activated marker molecules.

In order for the subset $1\_n$ to overlap as few diffraction disks as possible such that the marker molecules cannot be distinguished any longer, the activation energy shall be adjusted such that the subset $1\_n$ represents only a relatively small portion of the overall number of marker molecules so that statistically many marker molecules can be distinguished in reference to a volume that can be dissolved by the optic arrangement.

In a fourth step S4 the location of the fluorescent marker molecules is determined by way of calculation from the diffraction distribution of the fluorescent disks, by which the resolution disclosing the position of the marker molecules that can be activated is sharpened beyond the resolution of the optic arrangement, as shown in the detail c of FIG. 4.

Alternatively to the calculated determination it is generally possible to enhance the recorded fluorescent radiation in a non-linear fashion and this way to enhance the resolution beyond the optic arrangement with lesser expense. The non-linear enhancement may be performed, for example, according to the function $S=A*F^N$ (equation 1) or $S=A*\exp^{F/w}$ (with $w=10^{-N}$ (equation 2)), with F representing the amplitude of the fluorescent signal, A a norming factor, and N an integer greater than 1. A strong non-linear dependency of the parameter S from F is particularly advantageous, thus, e.g., high values for N in the equations 1 or 2. Of course, other functions may also be selected. In general, the non-linearity is preferably selected such that the half-width of the diffraction disk is equivalent to a desired spatial resolution for the determination of location of the marker molecules. In addition to a non-linear enhancement, a non-linear damping may also be used. Here, fluorescent signals with low amplitudes or intensities are damped, while strong signals remain at least largely undamped. Of course, any combination of non-linear enhancement and damping may also be used.

A fifth step S5 combines the marker molecules, with their statement of location being determined more precisely, to form an individual image, with its spatial resolution being enhanced beyond the optic resolution. However, it only includes information regarding the previously activated subset of the marker molecules.

In a sixth step S6 the individual image is inserted in a manner known per se into an overall image. Subsequently it is returned to step S1, with the previously fluorescent molecules now having to be deactivated. A deactivation may occur depending on the marker molecule by a separate radiation or by the activated state fading. Additionally it is possible to bleach already displayed marker molecules by way of exciting radiation.

With each run another individual image is yielded, contributing to the overall image. In the next run, another subset of the marker molecule is activated, e.g., the subset $1\_n+1$ shown in FIG. 4.

By the repeated run through the steps S1 through S6 the overall image of individual pictures of these individual runs is composed, which state the location of the marker molecules with a spatial resolution which is sharper compared to the resolution of optic imaging. By a respective number of iterations this way a high-resolution overall image is generated successively. The reduction of the diffraction disk here occurs in the method preferably in all three spatial dimensions when several image stacks distanced in the z-direction are recorded. Then the overall image comprises the high-resolution local information of the marker molecules in all three spatial directions.

Figure 5:
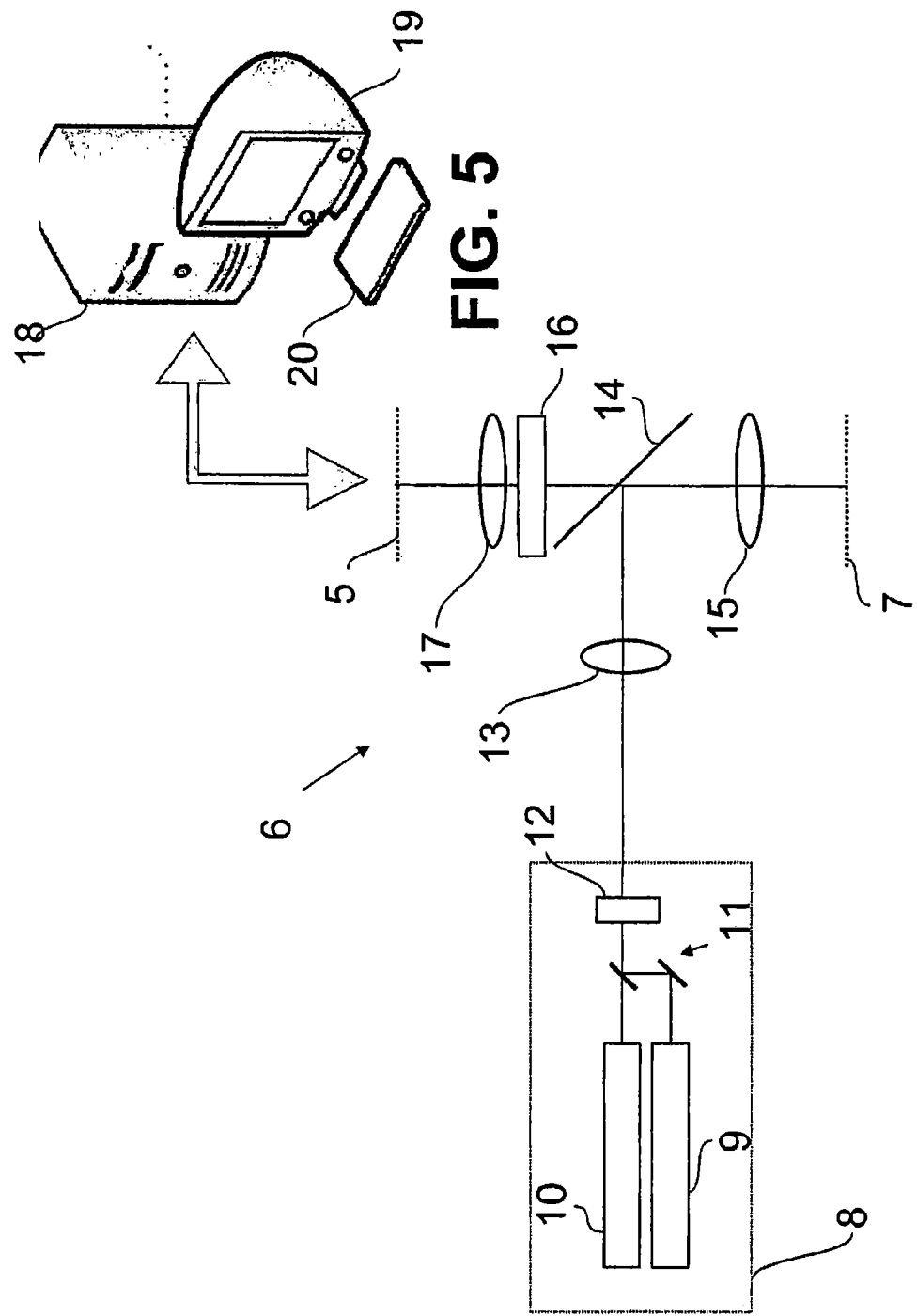
FIG. 5 is schematic illustration of a microscope concerning PAL-microscopy.

FIG. 5 shows schematically a microscope 6 for a high-resolution imaging of a sample 7. The sample is marked, for example, with the colorant DRONPA (cf. WO 2007009812 A1). In order to activate as well as to incite fluorescence the microscope 6 comprises a light source 8, which has individual lasers 9 and 10, with their radiation being combined via a beam combiner 11. The lasers 9 and 10 may, for example, emit radiation at 405 nm (activation radiation) and 488 nm (fluorescent excitation and deactivation radiation). Additionally, colorants are known (e.g., the colorant named DENDRA (cf. Gurskaya et al., Nature Biotech., Volume 24, pages 461-465, 2006)), in which the activation and excitation of fluorescence can occur at the very same wavelength. In this case one laser is sufficient.

An acoustic-optic filter 12 serves for the selection of wavelengths and for a rapid switching or dimming of individual laser wavelengths. An optic 13 focuses the radiation via a dichroitic beam splitter 14 in an aperture diaphragm of the lens 15 so that the radiation of the light source 8 impinges the sample 7 as a wide-field illumination.

The fluorescent radiation developing in the sample 7 is collected via the lens 15. The dichroitic beam splitter 14 is designed such that it allows the fluorescent radiation to pass so that it reaches a tubular lens 17 via a filter 16, so that overall the fluorescent sample 7 is displayed on the detector 5.

In order to control the operation of the microscope 6 a control device is provided, here embodied as a computer 18 with a display 19 and a keyboard 20. The processing steps S2 to S6 occur in said computer 18. Here, the image rate of the matrix detector is decisive for the overall measuring period so that a matrix detector 5 with an image rate as high as possible is advantageous in order to reduce the measuring period.

The reference characters in FIGS. 6-11 represent the following:
Pr: sample
O: lens
D, D1, D2, D3, D4: dichroitic beam splitter
L1-L2: light sources
Bt1, Bt2: image splitter module (detection on several levels)
K1, K2: area receiver (camera)
S Scan module (schematic) with X/Y scanners
Sx: one-dimensional scanner (in the x-direction)
TL: tubular lens
SO: scan lens
SLM: spatial light modulator
G: grid or grating
SML: micro-lens array
SE: single sensor of a sensor arrangement
B1, B2: adjustable slit diaphragm
Ld1, Ld2: line detector
ZL: anamorphotic optic, such as a cylinder lens
SF: beam splitter for linear focus (anamorphotic optic)

Most drawings have in common that, similar to the situation described in FIGS. 6-10 using the example of the PAL-M method, a first laser L1 may be provided for switching (activating) the colorant and lasers L2, L3 are provided for exciting fluorescence/deactivating colorants in the sample Pr in the wide field and one or more cameras (preferably CCDE) are provided for wide-field detection.

Included in the disclosure are further processes for a time-related activation/deactivation of colorants to generate high-resolution microscopic images of prior art as described at the onset.

Figure 12:
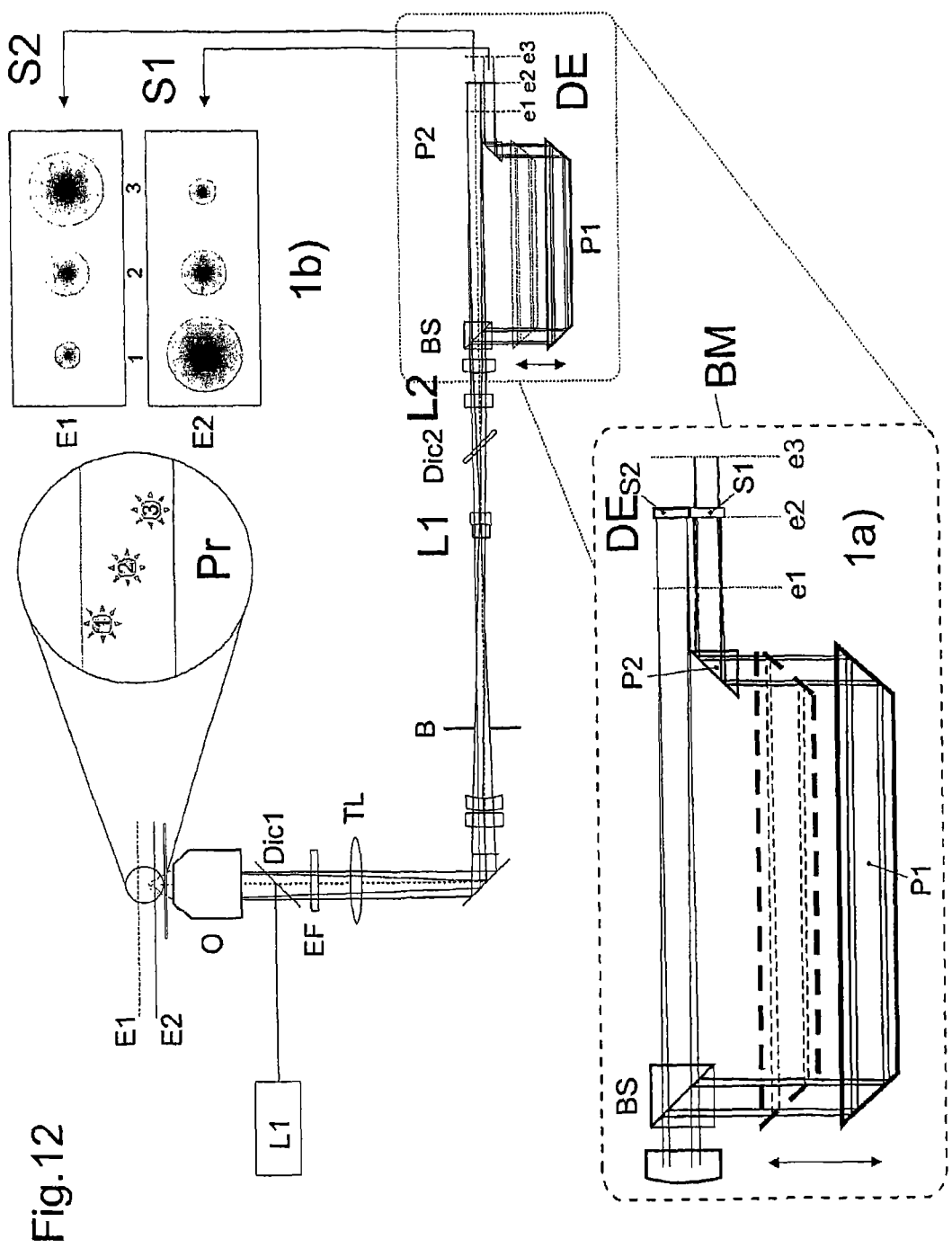
FIG. 12 shows a wide-field radiation path with a widened light source and a spatially resolving area detector, for example a CCD camera, together with an enlarged detail of the variable image splitter module BM according to the invention and enlarged, views show point images of molecules 1, 2, 3.
Figure 13:
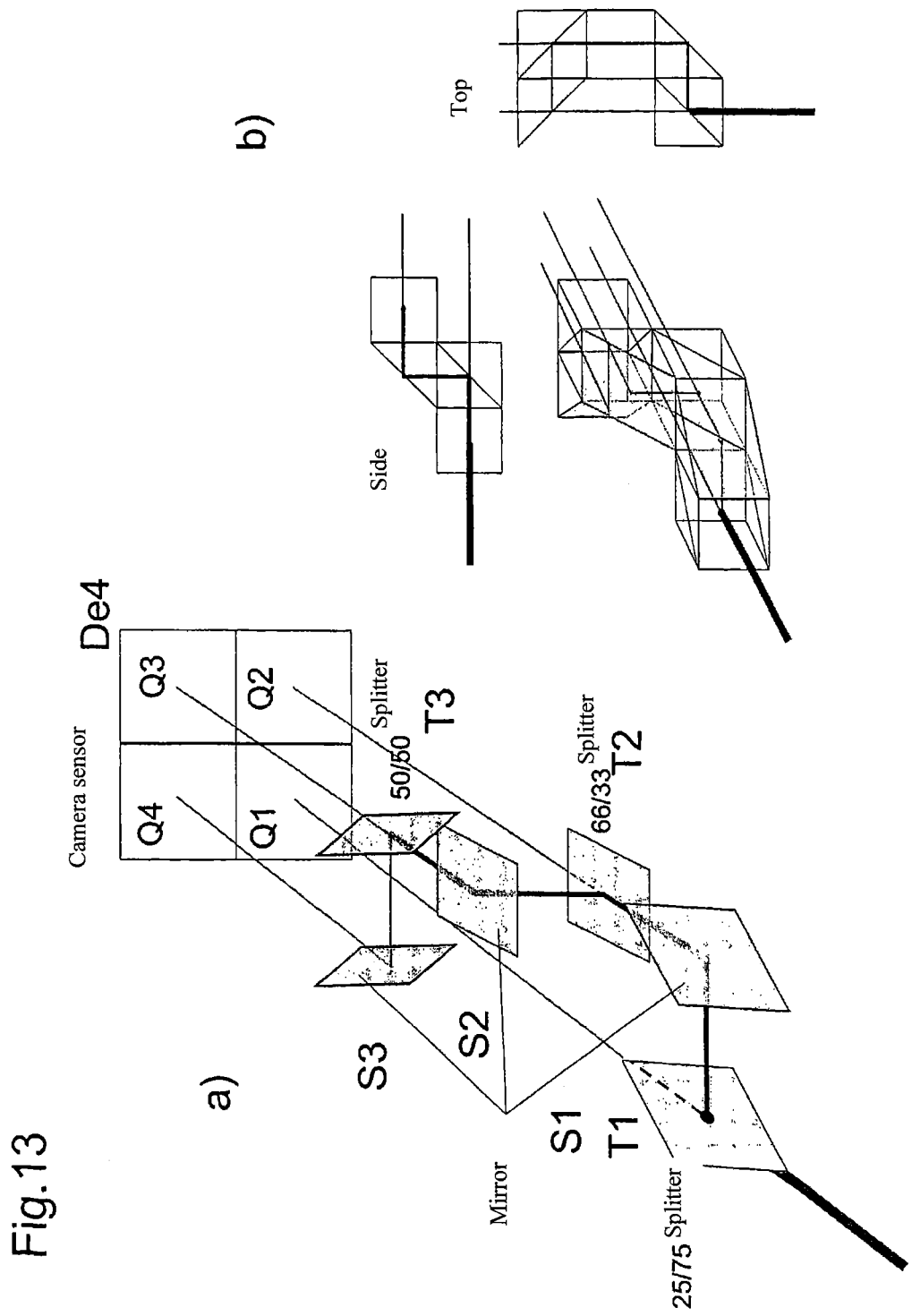
FIG. 13 shows an enlargement of four images of four sample levels, together with an area a) that shows an embodiment of a module for splitting a camera image into 4 partial images of identical intensity for z-high resolution, and an area b) that shows a monolithic embodiment with 3 beam splitter cubes.
Figure 14:
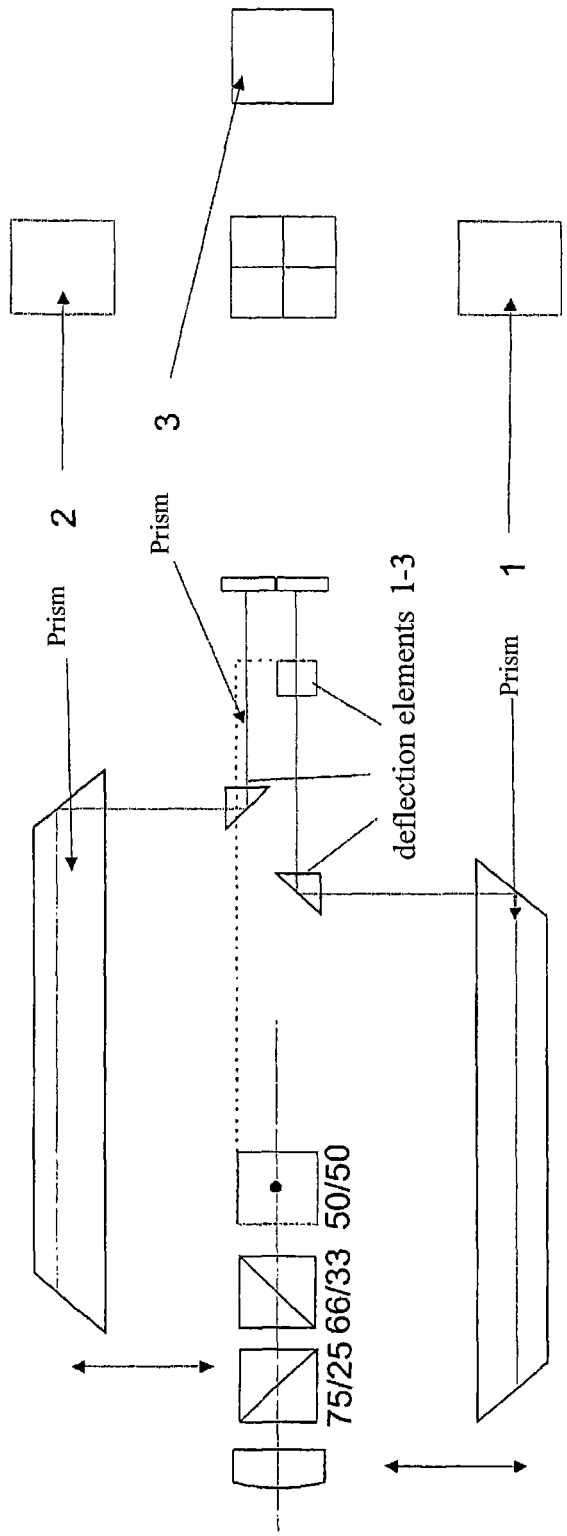
FIG. 14 shows an advantageous combination of an embodiment according to FIG. 13 with displaceable prisms according to FIG. 12.

Multi-level detection is understood as, for example, particularly an image splitter module according to FIGS. 12-14, and/or an anamorphotic illustration as well as embodiments of prior art (see literature items [7, 8]).

Here, "ROI," regions of interest, are considered regions, automatically or manually preselected for example based on an overview image, which can be impinged selectively with radiation.

Bi-Planar Detection Diagram with 2P Switching Using Point Scanners

Figure 6:
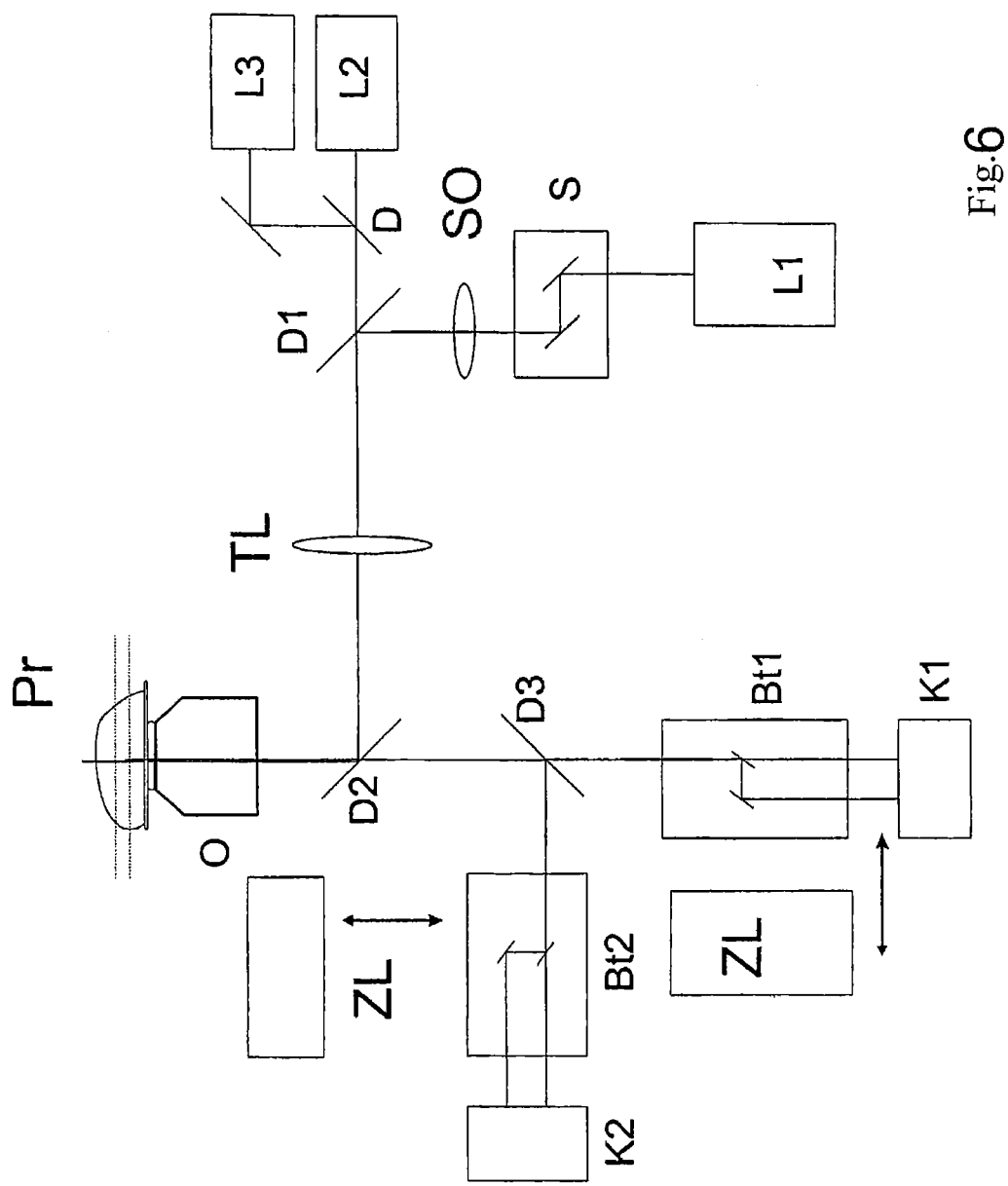
FIG. 6 schematically shows a depth-selective 3D-high-resolution fluorescence microscope (schematically) in a 2-channel embodiment.

FIG. 6 schematically shows a depth-selective 3D-high-resolution fluorescence microscope, in a 2-channel embodiment for 2 different fluorophores, simultaneously observed, comprising two cameras K1, K2.

A point-scanning scan module (S) follows, in the direction of radiation, a laser (L1) to switch via a non-linear excitation, particularly 2P excitation, which may be a ps laser diode or even a cw diode laser in the range of 780-830 nm (or another wavelength suitable for the 2P switching process); the laser L1 is coupled into the radiation path via the dichroit D1.

Lasers for the wide-field excitation L2 and L3 in various wavelengths are coupled via D into the radiation path. The detection of fluorescence occurs via D2 in the transmission in the direction of the cameras K1, K2 with a splitting into two color channels for different wavelengths of two fluorophores via D3. For each color a splitting of the image via image splitting modules (Bt1 and Bt2) can occur as described in FIG. 12-14.

Here, advantageously a fluorescence excitation occurs by laser wide-field illumination as well as wide-field detection by (sensitive) cameras, such as is common in PALM and similar localization-based high-resolution methods.

The detection occurs here beneficially with a biplanar (multi-level) detection diagram, (see items [7, 8]), FIGS. 12-14 for the highly precise localization of the molecules, also on the z-axis.

Here, the image is advantageously (see. FIGS. 12-14) split by the image splitting module (Bt1/2 in FIG. 6) such that two partial images develop with half the intensity each, with their conjugated object levels being off-set by, for example, approx. half the axial PSF.

These partial images are displayed side-by-side on the camera sensor (K1/K2) and can be assessed accordingly [7, 8] in order to determine the respective z-position of the individual fluorophores from the 2 partial images.

A particularly beneficial embodiment of this image splitter module is the object of FIGS. 12-14 with the following advantages:
Telecentric
No changes of the display scale as a function of the z-position
Parallel impingement upon the detector (→ no z-dependent distortion of PSF)
Adjustable z-splitting and thus ability to adjust to different lenses and embedding media
Ability to adjust the splitting to zero, whereby
The reference image level may be located on the sample surface; the adjustable splitting then occurs into the sample (and not into the cover glass as in embodiments of prior art)
Ability to remove the splitting in order to utilize normal camera images with a full sensor.

It is particularly advantageous for the range of depth of focus achieved by the described image splitter module according to FIGS. 12-14 to be variably adjusted to a similar range as the minimal layer thickness of the two-photons excitation (for example, 700 nm) and/or as shown in the arrangement according to FIGS. 12-14. Here, an optimal overlap develops of an activated (=switched) layer and a layer measured with high-resolution.

The switching (photo-converting) of the fluorophores from their non-excited into their excited state (condition for PALM) occurs here via a focusing, point-scanning excitation beam, with its wavelength being selected such that the switching process occurs by a 2-photon (or 3-photon, generally multiphoton) absorption process, while the fluorescent excitation and detection of the fluorophores switched in this manner occur in the wide-field.

Based on the stochastic activation of the photo-switches in the PALM method the grid-based activation is not necessarily synchronized with the imaging of the camera.

The 2P switching (converting) beneficially leads to the "sectioning" known from the 2-photon microscopy, thus the selective excitation of only the molecules in the focal area. This way a z-resolution can be achieved similar to the confocal microscopy without the use of any confocal pinhole being required. This way the method can easily be combined with the camera-wide-field detection required for PALM.

Additionally, contrary to the confocal detection, any out-of-focus switching is avoided, which is particularly important for the imaging of high-resolution z-stacks.

It is known that the photo-conversion (the switching) of the typically used photo-switches for PALM microscopy requires extremely low intensities only. Accordingly the 2P effect can also be achieved with cost-effective cw lasers, beneficial in reference to expensive short-pulse lasers for 2P microscopy.

For fluorophores or applications and/or sample preparations requiring higher power for the 2P switching process, a laser diode operated in the pico-second mode (exemplary embodiment) may be used or other, cost-effective ps laser systems.

The typical 2P switching wavelengths for common PALM fluorophores range from 760-850 nm, a range well covered with cost-effective semiconductor lasers.

In FIG. 7, in a), an adjustment occurs of the switching intensity of the point-scanned switching laser to the marking density in the sample. In the area I marked thinner the switching intensity is increased in order to adjust the rate of the localized molecules to the one in the denser marked area II." FIG. 7*b* shows a schematic image stack in the x-z cross section.

By a targeted switching of the scanned activation laser in only two previously manually or automatically defined ROIs the undesired switching above or below the just detected layer is avoided. This is particularly advantageous when recording z-stacks comprising several such layers.

Using the point-scanned switching beam ROIs (regions of interest—see DE 19829981A1 can be defined, with fluorophores being activated therein; however, in TIRF-PALM all regions of the sample are always activated. This way, the method described here, e.g., the switching intensity within a frame, can be optimally adjusted to the marker density of the sample (cf. FIG. 7*a*)). This way, the imaging period can be reduced, which is important, particularly for taking images of 3D-image stacks. Additionally, the localization rates can also be adjusted to other fields in the sample marked with different fluorophores.

Another advantage comprises that undesired switching of molecules in sample fields above and below the z-layer most recently to be recorded can be minimized (in addition to the above-mentioned intrinsic sectioning of the 2P excitation), by the activation radiation exclusively being switched on in the sample fields with colored structures (FIG. 7*b*)).

In principle, both effects can also be achieved with the classical 1P switching source, when it is focused and scanned. However, the very beneficial sectioning of the 2P absorption is not achieved, here.

An advantageous method for a sequential process for a numerically controlled feedback for 2P switching can occur according to the invention.

In inhomogeneously colored samples it allows a quicker achievement of the comparable localization density in different sample fields and thus a faster recording time.

After the recording of the camera image (optional: real-time localization) a determination occurs of the number or number density of the localized molecules per ROI as well as a comparison {area ROI: number} with the PSF in such a way:

When {area ROI: number}>>is (larger than) the PSF the intensity of the 2P switching beam for this ROI is increased.

When {area ROI: number}~=is (in the area) of PSF, the intensity of the 2P switching beam for this ROI is reduced.

The issue of the respective intensity modulation to the scanning 2P switching beam follows and a subsequent camera image is recorded.

A Method According to the Invention for ROI-Controlled Feedback for 2P Switching:

minimizes the undesired switching of molecules in the sample fields above and below the just measured sample level by the following steps:

Defining one or more ROIs automatically or manually based on a first image, recorded with high switching and/or excitation intensity, or based on an image obtained with other contrast functions (DIC)

Issuing the respective intensity modulation on the scanned 2P switching beam so that the switching radiation is "on" only within a predetermined ROI Within these predefined ROIs, similar to 9.3.2, the adjustment of the switching intensity can occur to the count rate of the molecules.

The described regulation of the switching intensity is particularly advantageous for samples colored with different fluorophores, which are measured simultaneously.

For example, perhaps different switching rates of different molecules can be adjusted by the spatial adjustment of the switching intensity and this way the recording period for multi-color measurements can be reduced. The ROIs can be defined based on sample characteristics or can be superimposed over the image as a regular grid with fields of a suitable size; the latter is particularly advantageous for the following explanations with wide-field switching illumination (temporal focusing, spinning micro-lens disk).

Bi-Planar Detection Diagram with 2P Switching Using Line Scanner

In order to achieve sufficient activation of a stochastic subset of fluorophores per camera frame necessary for PALM, particularly for quick imaging rates, a very high scanning speed of a point scanner is required. The use of a line for the 2P switching accordingly reduces the scanner speed. The reduction of the peak intensity allocated to the line can be tolerated due to the low switching intensities necessary.

Figure 11:
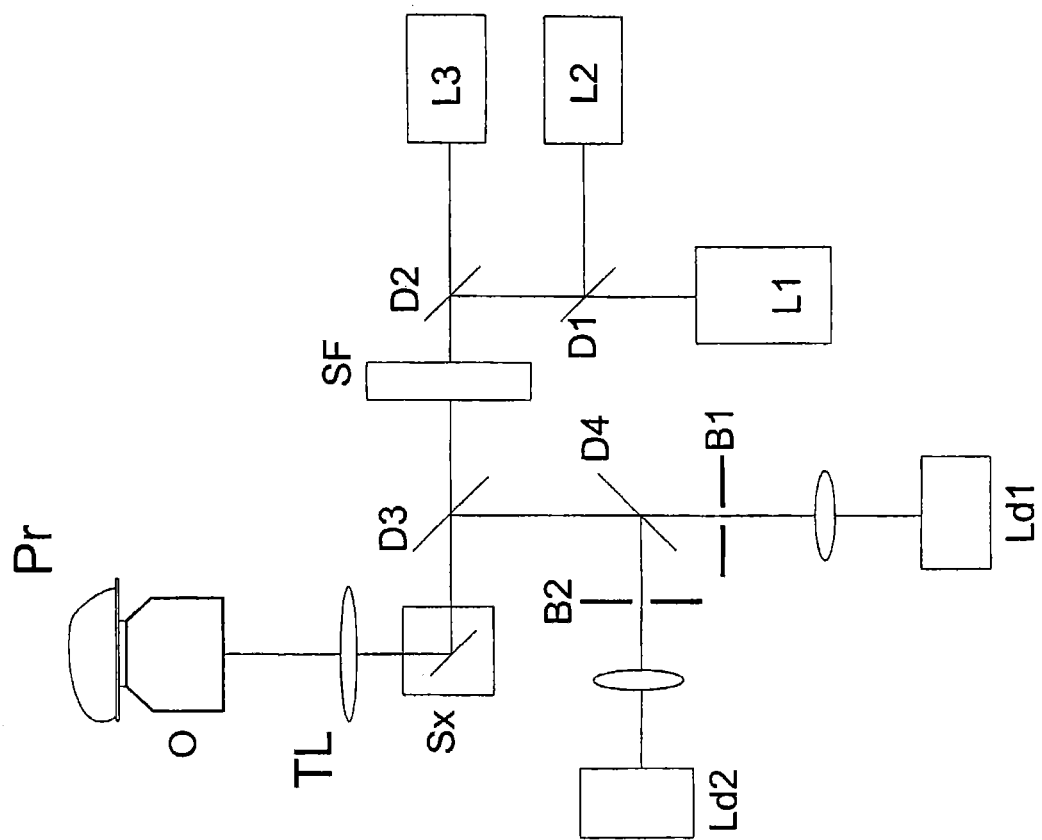
FIG. 11 shows schematically a potential embodiment of a depth-selective high-resolution microscope based on the sensor principle.

Instead of a point scanner, a line scanner can also be used for 2P excitation in FIG. 6 (see also FIG. 11)

The low intensities required for switching colorants also render the use of a scanned line possible in connection with the 2P switching process.

This line may be created with an anamorphotic optic, for example, and moved with a one-dimensional scanner through the object.

Here, the advantage lies in the fact that a more rapid scanning is possible, because only 1D-scan is required.

Due to the fact that the activation occurs stochastically and the detection occurs in a wide field it is not necessary for the line to be synchronized with the imaging process.

Bi-Planar Detection Scheme with 2P Switching Via Temporal Focusing

Figure 8:
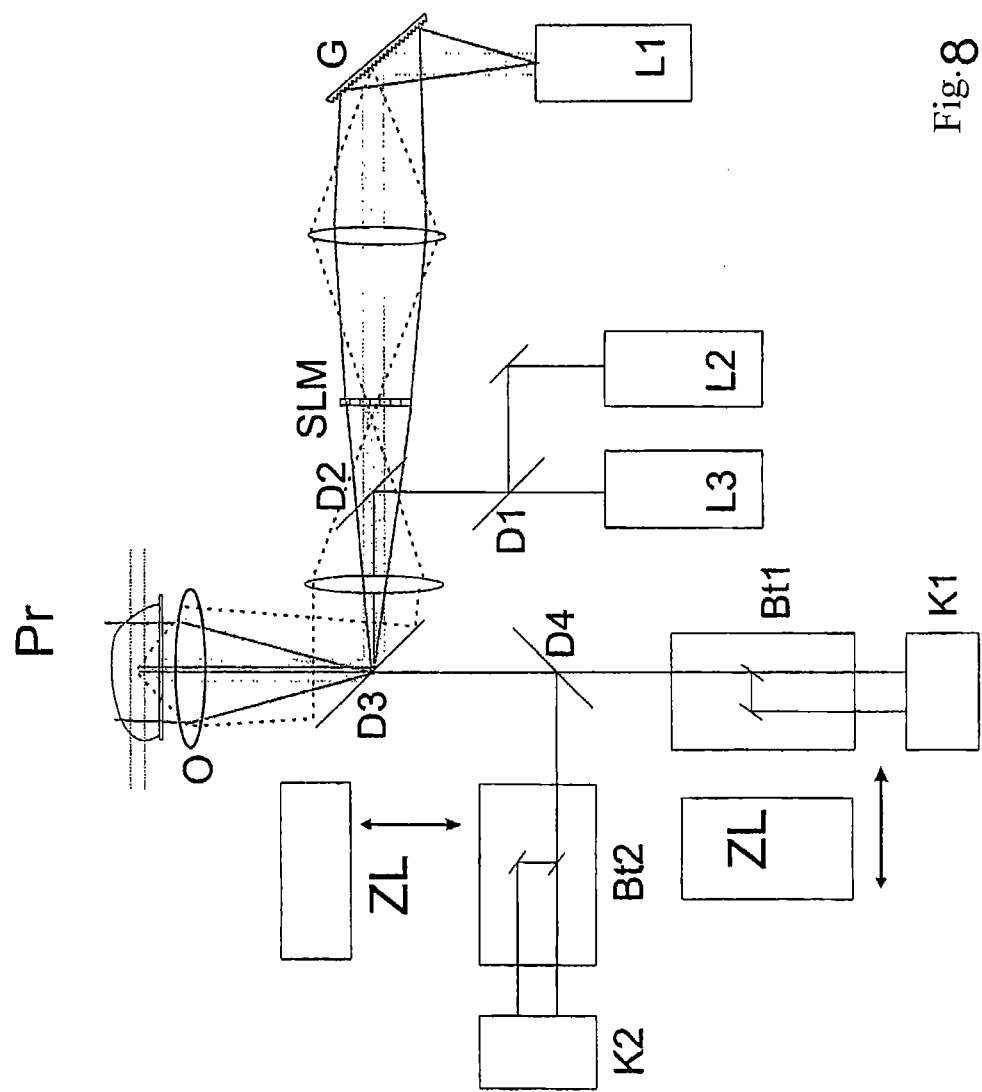
FIG. 8 schematically shows a depth-selective 3D high-resolution microscope.

FIG. 8 schematically shows a depth-selective 3D high-resolution microscope with L1 as the activating laser; L2, L2 as the excitation laser, a grid G: grid; a SLM: spatial light modulator (see here for example DE 19930532A1); D1-D4 are dichroitic beam splitters and/or combiners, Bt1 and 2: image splitter modules, K1 and K2 here represents cameras.

Figure 8A:
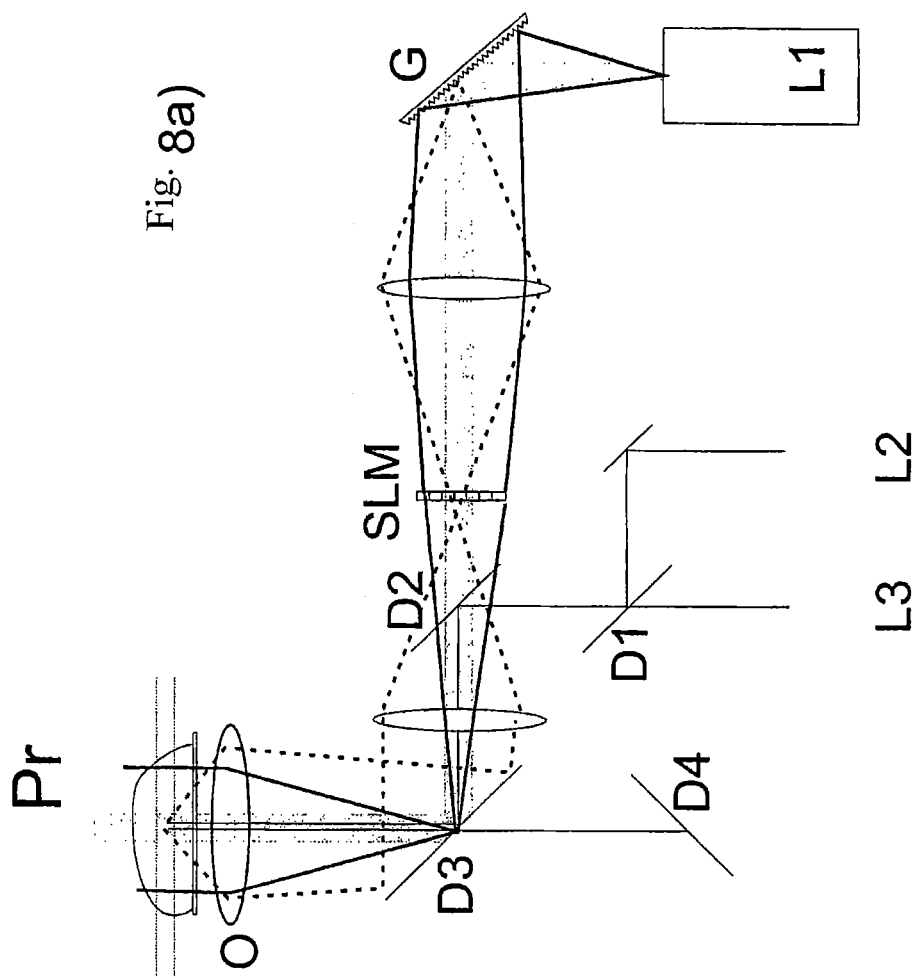
FIG. 8(a) shows the radiation beam from the light source to the sample in an enlarged fashion.

FIG. 8a shows the radiation beam from the light source to the sample in an enlarged fashion.

The radiation path is shown with a continuous line and the image [thereof] in dot-dash lines.

Figure 9:
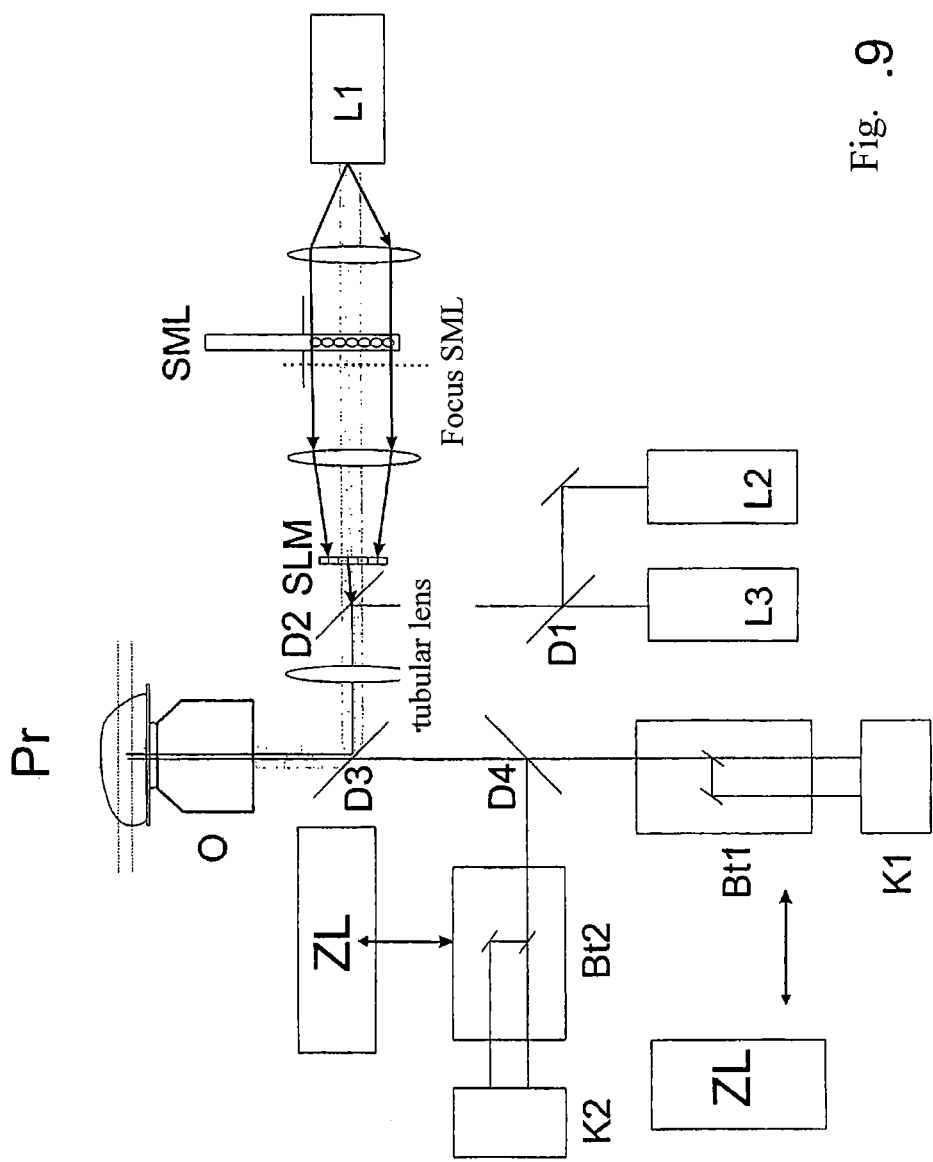
FIG. 9 schematically shows a depth selected high resolution microscope with a scanning micro-lens dish.

This also applies respectively for the illustration of FIG. 9.

The lens arrangement O is shown schematically by a lens.

The grid is located in an interim image and is displayed in the next interim image (dot-dash lines) in which the SLM is located. This in turn is displayed in the sample.

However, the radiation bundle (continuous line) of the laser is "off-set"; in the sharp interim images (grid, SLM, sample) the illustration spot is maximally unfocused, here.

Here, once more a ROI functionality can occur as described above, with the difference that the respective switching intensity is now adjusted via the SLM in the interim image.

This arrangement advantageously operates without any moving parts (non-scanned) and yields similar flexibility as the above-mentioned scan arrangement.

The depth selection is now achieved via the 2P switching effect in connection with the temporal focusing [11 and references therein]. For this purpose, using the widened beam of a short-pulse laser L1 with a wavelength suitable for the 2P excitation of the switching process, a grid G is radiated. The radiated field of the grid is then displayed in the sample. The grid splits the spectral portions of the laser pulse such that the original short pulse form is achieved only in the focus of the display (and perhaps interim images) and accordingly only the high peak intensities are provided for the 2P activation process.

As shown in (11), in a telescopic radiation path a reconstruction of the short pulse only occurs in the sample (the image level of the telescope).

An SLM as the modulator for the split wavelengths is positioned in an interim image of the display, with here the original pulse form being reconstructed.

ROI is created by a selective switching of the SLM elements.

Here, the ROI functionality can now also occur in the wide-field excitation (in addition to the switching). For this purpose, the laser wide-field excitation must also be guided through the SLM or be given a separate SLM; then even the separate definition of ROIs for excitation and switching is possible. This embodiment is shown in FIG. 8 for the case of a 2-color excitation and detection.

Alternatively to the SLM, a DMD (digital micro-mirror device) array may also be used. The design is similar to FIG. 8, however now the DMD array must be used in a reflection (again in an interim image).

Astigmatism/cylinder lens detection diagram with 2P switching by point scanner

The design is equivalent to FIGS. 6, 8, 9, however with cylinder lens(es) ZL in the detection radiation path instead of Bt1 and/or Bt2.

This is optionally marked in FIGS. 6, 8, 9 by an arrow.

Bi-Planar Detection Diagram with 2P Switching Via Rotating Micro-Lens Disk

FIG. 9 shows a depth-selective 3D high-resolution microscope (schematically) with a scanning micro-lens disk (SML). The references are equivalent to those in FIG. 8.

The irradiation occurs by 2P laser L1, for example at approx. 800 nm (e.g., ps laser diode). After the beam adjustment to a micro-lens array (scanning micro-lens array) (SML) the foci of the (rotating) micro-lenses are displayed in the sample via an interim image with a SLM located therein. This way, a rapidly scanned 2P point source is realized for switching the fluorophores with ROI-functionality via the SLM.

Additionally, a decoupling of the laser wide-field irradiation occurs to excite the fluorophores via dichroit 1 (D1). Detection and z-information are according to the above examples.

Advantages are:
the speed
and the confocal depth discrimination at wide-field radiation, combined with
ROI functionality by SLM or DMD.

Confocal High-Resolution Microscope with Line Scanner

In principle, the localization-based high-resolution methods described cannot be performed with a standard LSM: the sub-PSF-precise localization must occur by the simultaneous spatial oversampling by the camera pixels, because the molecules are fluorescent only for a limited period of time and/or activated (stochastically) at unpredictable points of time. Therefore any method is excluded in which the focal point of the molecule is determined sequentially (grid method).

In the wide-field imaging as practiced in prior art again the desired depth selection is missing by a confocal illustration of a LSM.

The arrangement presented here comprising a particular line sensor (FIG. 10) and a respective microscope (FIG. 11) allows, however, the advantageous combination of confocal line scanning and localization-based high-resolution and this way allows a PALM-similar high-resolution microscopy method in connection with the depth selection of a confocal microscope.

In order to increase the penetration depth the line radiation for switching and/or excitation can also occur by a multiphoton process.

This approach differs from the one of FIG. 6 such that here depth selection is achieved by a confocal line display.

Figure 10:
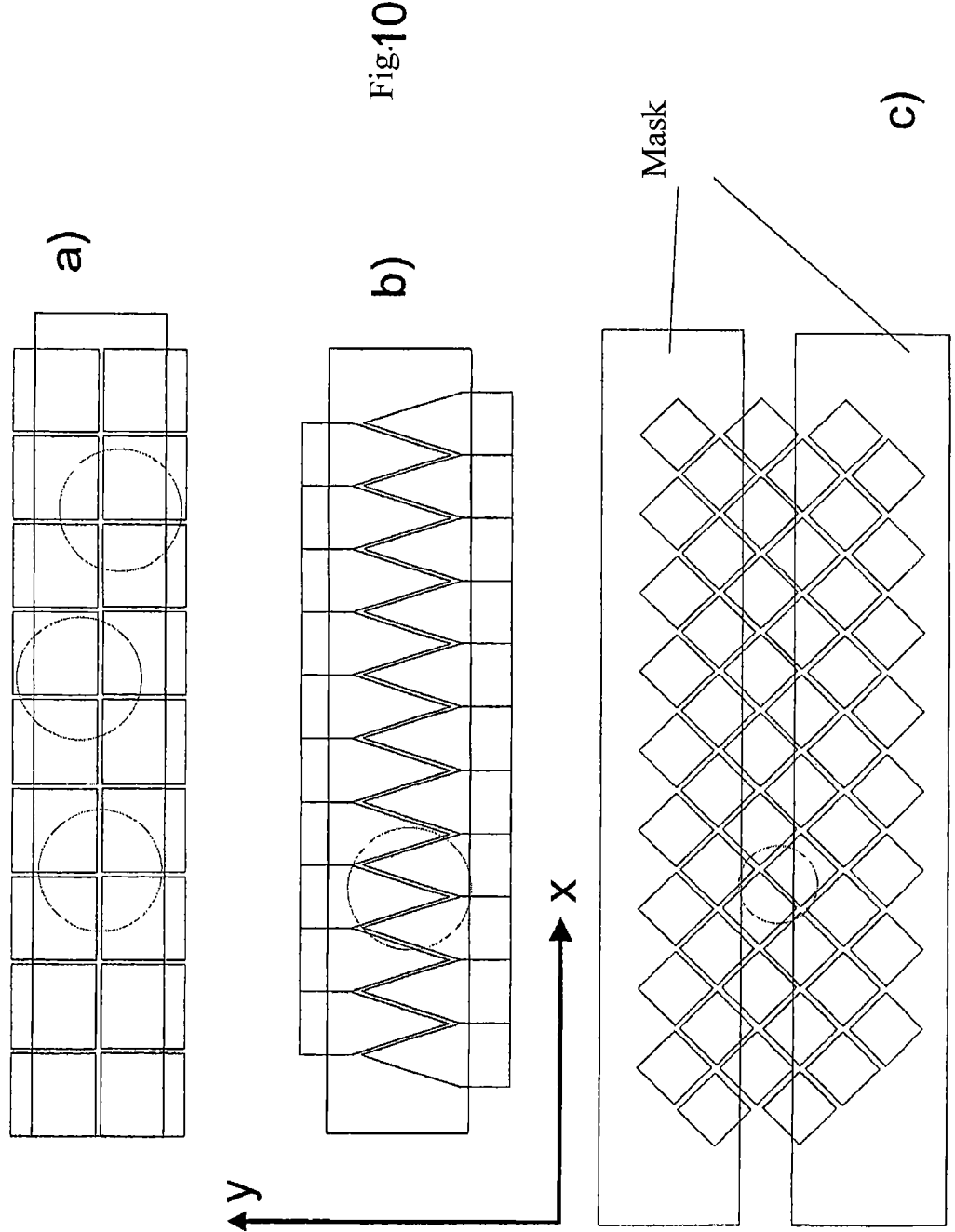
FIG. 10(a) shows a principle of the localization-based confocal high-resolution microscopy with a line sensor.
FIG. 10(b) shows a sensor with an engaged pixel structure.
FIG. 10(c) shows an example to realize an engaged pixel structure with existing pixel geometries by way of masking.

FIG. 10: a) shows a principle of the localization-based confocal high-resolution microscopy with a line sensor, 10 b) a sensor with an engaged pixel structure, 10 c) an example to realize an engaged pixel structure with existing pixel geometries by way of masking.

FIG. 10 a) explains the principle based on a 2-line sensor (for example the sensor of a cell camera as frequently used in machine vision).

The lateral localization (along the cell direction) can occur as known from focal imaging or fitting a suitable function (1D Gauss), in which the engaging pixels of both cells are to be considered, here. The localization orthogonally in reference to the line direction can occur by forming the difference signal of the respective pixels of the opposite row of pixels. The principle is here equivalent to a position-sensitive detector (PSD). In order for the PSD-function to be ensured the confocal slit diaphragm must be opened slightly wider than one airy unit.

The different precisions of localization in the x- and y-direction which might develop from this approach can be adjusted by an alternative sensor design. FIG. 10 b) shows a potential sensor structure with two engaging combs.

Here, for the determination of the y-coordinate, first the determined x-position must be evaluated and considered, because by the engaged pixel structure the PSD-function (y-focal determination) depends on the x-position of the molecule to be localized.

The image of the line shall be selected such that the PSF-width is precisely equivalent to the width of a pixel line; however it is centered to the middle of the engaging comb-like structure.

FIG. 10 c) shows an alternative suggestion for realization based on quadratic pixel geometries of prior art. Here, for example a normal sensor can be rotated by 45 degrees in order to yield this pixel orientation. In principle, an area sensor may also be used for this purpose, which is masked except for the desired line of detection. This mask can also be embodied as a variable diaphragm.

According to the invention several, advantageously two, rows of pixels are used for assessment. In 10a)-c) one molecule is schematically drawn in dot-dash lines, which is detected by several detector elements.

For this purpose, the existing slit diaphragm in a line scanner is opened slightly in order to simultaneously detect two rows. In 10a and b the slit image is shown, detected here.

As an example, FIG. 10c) shows the detected area slightly lighter than the area masked, located above and below this.

By the mutual subtraction of advantageously four detector elements, which are located side-by-side of each other and each detecting a signal, the focal point of the detected molecule can be precisely determined (by the amount and algebraic sign of the result of the subtraction).

Added here is depth information comprising form and size, for example using the above-cited method.

FIG. 11 shows schematically a potential embodiment of a depth-selective high-resolution microscope based on the sensor principle.

FIG. 11 shows a depth-selective 2D high-resolution confocal microscope (schematically) with a line scanner, for example for two-color detection. Switching and excitation lasers (L1-L3) are brought into a linear form via a beam former (SF) and scanned in a spatial direction (scanner Sx). In the detection the line is confocally displayed by appropriate slit diaphragms on the line detectors (Ld1, Ld2), as described in the above text. D1-D4 are dichroitic beam splitters and/or combiners.

The line for irradiation is generated by the beam-forming optic SF (cylinder lens) and scanned in one spatial direction (scanner Sx). The fluorescence is confocally displayed via slit diaphragms B1 and B2 (here an exemplary embodiment with two color channels) to the line detectors Ld1 and Ld2 shown sketched in FIG. 10.

In FIGS. 12-14 advantageous variable image modules Bt1, Bt2 (see, e.g., FIG. 6) are sketched for z-splitting.

The reference characters represent in detail:
E1, E2: object levels
BM: image splitter module
O: lens
Dic1: primary color splitter
L1: light source
EF: emission filter
TL: tubular lens
SP: deflection mirror
B: diaphragm (telecentric diaphragm)
L1, L2: group of lenses
Dic 2: color splitter for optional masking
BS: beam splitting cube
P1 dual deflection prism, adjustable perpendicular in reference to the optic axis
P2 deflection prism
DE wide-field detector
S1, S2: sensor halves
e1, e2 image levels FIG. 12 shows a wide-field radiation path with a widened light source and a spatially resolving area detector, for example a CCD camera.

The light of the light source L1 reaches (reflected) the sample Pr via Dic 1 and the lens O. The reflected and fluorescent sample light travels via the lens towards detection.

At the splitter Dic 1 and via the filter EF a selection occurs of the desired light, here a suppression of the reflected light; i.e. only the fluorescent light travels in the direction of detection.

Via SP, L1, L2 the sample light reaches the arrangement according to the invention comprising BS, P1, and P2 and then the detector DE.

E1 and E2 are different object levels in the sample Pr.

FIG. 12a shows an enlarged detail of the variable image splitter module BM according to the invention. An image of the sample Pr is split via the beam splitter cube BS into two partial images on the detector DE. The prism P1 is displaced in a motorized fashion perpendicular in reference to an optic axis in order to adjust the splitting of the two object levels. Via P2 (fixed) the displaced partial image in turn is reflected into the penetrating radiation path, spatially displaced in reference to the penetrating radiation path, i.e., laterally off-set in reference to DE.

Based on the image levels e1-e3 and the very same object level in Pr, for example E1, the invention is explained in greater detail:

The dot-dash position of P1 indicates the shortest possible position of BM; the image level e3 yielded here would be positioned behind the detector DE.

The image level e2 of the partial image, not deflected, is located on the sensor (partial image S2 of the sensor). By displacing the prism P1 towards the outside into the lower position in FIG. 12a the path is extended and the image level e1 moves (opposite the radiation path) towards the front. Here, it follows that an object (molecule) located in the object level E2 is displayed focused on the sensor half S2 and blurred on the sensor half S1. This applies equivalently for an object located in the object level E1 and/or between E1 and E2.

E1 would be focused on S1 and E2 would be focused on S2; everything else would be blurred using the same prism position.)

In FIG. 12b, in an enlarged fashion, point images of molecules 1, 2, 3 of the object levels E1, E2 are each shown on the sensor halves S1 and S2.

It is discernible that in E1 and E2 molecules (1 in E1 and 3 in E2), each arranged in different levels, are detected focused in S1 (molecule 1) and S2 (molecule 3), while molecule 2 respectively is detected blurry because it is obviously located between E1 and E2.

Therefore, from the size of the molecules on the detector sections deductions can be drawn concerning their precise location in the z-direction in the sample.

Additional radiation paths of two molecules are indicated in the drawing, with both of them being located in the object level E2.

The diaphragm B defines the detail reduced by half (equivalent to the size of the sensor halves S1 and S2) and prevents light from outside this area from impinging the two partial radiation paths.

The splitting into two partial images occurs at the 50/50 radiation splitter cube BS.

The objective to focus the undeflected partial image into an image level different from the directly displayed partial image is fulfilled by the prism P1. This prism P1 extends the focus of the respective bundle compared to the respective path through the air; therefore it shall preferably be embodied from highly diffractive glass, in order to obtain an operating range as large as possible. These bundles are then once more directly reflected via the prism P2 parallel to the direct radiation path and deflected to the image sensor DE in section S1.

With the focal extension after the last optic/lens L2 in the prism P1, by selecting the length of the prism, it can be ensured that, in spite of a mandatorily longer radiation path of the deflected partial image, both partial images of different object levels E1, E2 are simultaneously displayed focused on the detector DE.

By displacing the prism P1 perpendicular in reference to the optic axis of the direct radiation path the z-displacement of the focal areas of the two partial images of different object levels can be adjusted in the sample.

This way, the splitting can be advantageously adjusted, for example, to different lenses.

This is possible without any secondary focusing of the system, because the system has been designed such that an adjustment of "zero" can be set and particularly when observing the surface of the cover glass the second focal area can be moved into the sample (and not into the cover glass).

In another arrangement, in which the glass path of the prism P1 is waived and only two deflection mirrors are used, jointly displaceable perpendicular in reference to the optic axis, two different object levels can also be displayed focused advantageously on two different object levels on the camera.

However, due to the lateral path the zero compensation would not be achieved and with the lateral displacement of the mirrors it would further move into the "cover glass." In order to vary the second object level in the sample space then the splitting of the object level would have to be adjusted via the mirrors and then refocused at the lens such that the cover glass is once more focused via the deflection on the detector. However, this arrangement described is still within the scope of the invention disclosed here.

An exchange of the prism P1 for another prism with different glass paths is possible, according to the invention.

The illustration, from the object to the detector through the lens L2 in connection with the optic L1 left in reference to the beam splitter Dic 2 is overall advantageously telecentric.

An adjustable, preferably rectangular diaphragm B in an interim image serves to define a rectangular image area, split via P1, P2, for suppressing fluorescent and diffused light from the field ranges outside this new field.

For multi-color experiments a second emission wavelength can be deflected via the color splitter Dic 2 and by the use of a second, preferably identical z-splitting module and another detector this radiation path can also be used for high-resolution localization.

Potential errors of color length of the lens or other chromatic errors influencing the z-localization of the individual molecules can be compensated by adjusting the splitting for the second color channel.

FIG. 13a) shows another advantageous embodiment of a module for splitting a camera image into 4 partial images of identical intensity for z-high resolution.

In FIG. 13a left, an embodiment is shown with separate mirrors and beam splitters. A first splitter T1, here 25/75 splitting regarding transmission and reflection, guides a portion of the light to the area Q1 of the detector DE4.

A second portion is T1 reflected and guided via the mirror S1 in the direction of a second splitter T2 at a ratio of 66/33. It allows a portion of the light to pass in the direction of the area Q2 of DE 4 and reflects a portion in the direction of a mirror S3, which deflects the light in the direction of the 50/50 splitter T3. A portion passes through T3 to the area Q3 of DE 4 and a portion is deflected via S3 in the direction of the area Q4 of DE 4.

By the splitting of the z-levels in the monolithic design by one "cube length" each of a beam splitter cube four evenly displaced image and/or object levels develop, with the quadrant Q1 of DE 4 seeing the image in the direct passage, quadrant Q2 an image displaced by a "standard distance" (=one beam splitter cube length in the monolithic design, right), quadrant Q3 by two, and quadrant Q4 by 3 distances.

The splitter ratios of the 3 beam splitters shown here, without any limitation, ensure that all 4 quadrants preferably detect the same intensity.

In FIG. 13b a monolithic embodiment with 3 beam splitter cubes is shown for T1-T3 and 3 mirrored prisms for S1-S3 from the side, from the top, and in a perspective.

The arrangement in FIG. 3a) and b) is advantageously also suitable for a telecentric detection beam path as described according to FIG. 12.

The advantages of the arrangement according to the invention in FIG. 13 provides a more precise z-determination in a larger operating range. This is accomplished by four images of four sample levels so that four support points are provided for the z-determination.

The square sensor format of the high-sensitive EMCCD cameras is further used more efficiently.

In FIG. 14 an advantageous combination occurs of an embodiment according to FIG. 13 with displaceable prisms according to FIG. 12.

The right side shows a view from the direction of the sensor, the left one a top view.

Instead of the mirrors S1-S3, in FIG. 14 here prisms 1-3 are provided, which define a radiation path parallel in reference to the optic axis through a medium of higher optic density. Compared to FIG. 13 here additional deflection elements 1-3 serve to redeflect [the beams] into the respective partial radiation path.

Each of the three prisms 1-3, adjustable perpendicular in reference to the optic axis (direction of radiation), is provided for one quadrant Q2-4 of the sensor (FIG. 13); the fourth quadrant Q1 is irradiated by the direct passage. Each prism could now be adjusted to a different displacement of levels.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A high-resolution microscope for two-dimensional or three-dimensional determination of the position of objects, including individual fluorophores, for spatially high-resolution fluorescence microscopy of a sample, said high-resolution being beyond the optical diffraction limit, which sample is marked with marker molecules, which molecules can be activated or switched by a signal such that they can only be excited to emit fluorescent radiation in an activated or switched state, comprising:
1) means for introducing said signal to the sample such that only a subset of marker molecules provided in the sample are activated, with partial areas in the sample existing in which activated marker molecules are at least at a distance from the closest neighboring activated or switched marker molecules, which distance is greater than or equal to a length resulting from a predetermined optic resolution, said predetermined optic resolution including resolution beyond the diffraction limit,
2) means for exciting the activated molecules to emit fluorescent radiation,
3) means for detecting fluorescent radiation with said predetermined optic resolution, and
4) means for generating an individual image of said fluorescent radiation recorded in step 3), with the geometric location of the marker molecules emitting the fluorescence radiation being determined with a spatial resolution exceeding the predetermined optic resolution,
with the foregoing steps being repeated several times and a plurality of individual images resulting therefrom being combined to an overall image,
means for multi-plane detection by splitting the detection radiation in a Z direction, and at least one of the following:
a cylindrical lens arranged in an imaging beam path as an anamorphotic optic arranged in the display radiation path;
at least one beam splitter provided to split the detection radiation path into at least two partial radiation paths and the partial radiation paths comprise a spatial off-set in reference to each other in the detection plane;
a short pulse laser provided as the activating or switching source for non-linear sample excitation; and
a point scanner or a line scanner provided for non-linear excitation with said short pulse laser.

2. The high-resolution microscope according to claim 1, with, for extension of the optic path, at least a second portion of the detection light emitted by the sample being masked from the detection radiation path and guided via deflection means to the deflection radiation path in at least one second detection radiation path.

3. The high-resolution microscope according to claim 2, with at least a second portion of the detection light being redeflected via additional deflection means in the direction of detection such that at least two partial fields are impinged with detection light, side-by-side on an area receiver.

4. The high resolution microscope according to claim 1, with at least a second portion of the detection light extending at least partially in an optic element as an extension of the optic path with an optic density increased in reference to the first detection radiation path.

5. The high-resolution microscope according to claim 4, with the optic element adjustably arranged at an angle in reference to the optic axis of the first detection radiation path, to adjust the optic path, and comprising planar surfaces at least at its light inlet and light outlet sides.

6. The high-resolution microscope according to claim 1, with at least in a second detection radiation path, after a first beam deflection, a prism being provided, preferably a glass prism, for deflecting in a direction parallel in reference to the first detection radiation path in order to increase the path and to deflect back.

7. The high-resolution microscope according to claim 6, with the prism being penetrated by the parallel part of the second detection radiation path and preferably embodied displaceable perpendicular in reference to the optic axis for adjusting the optic path.

8. The high-resolution microscope according to claim 1, with a telecentric radiation path being provided from the sample to the detector.

9. The high-resolution microscope according to claim 1, with a splitting into four detection radiation paths occurring via partially permeable mirrors and deflection elements, offset in reference to each other and impinging one or more detectors, with preferably three partially permeable mirrors and three deflecting elements being provided for splitting and the partially permeable mirrors having splitting ratios of 25/75, 66/33 and 50/50 between transmitted and reflected radiation.

10. A high-resolution microscopy method for a two-dimensional or three-dimensional determination of the position of objects, including individual fluorophores, for spatially high-resolution fluorescence microscopy of a sample, said high resolution being beyond the defraction limit, which sample is marked with marker molecules, which marker molecules can be activated or switched in a signal such that they can only be excited to emit fluorescent radiation in the activated or switched state, said method comprising the following steps:
1) introducing said signal onto the sample such that only a subset of the marker molecule present in the sample is activated, with partial area existing in the sample in which activated marker molecules are at least at a distance from their closest neighboring activated or switched marker molecules, which distance is greater than or equal to a length resulting from a predetermined optic resolution, said predetermined optic resolution including resolution beyond the diffraction limit,
2) exciting the activated molecules to emit fluorescent radiation,
3) detecting fluorescent radiation with said predetermined optic resolution, and
4) generating an individual image from said fluorescent radiation recorded in step 3), with the geometric locations of the marker molecules emitting the fluorescent radiation being determined with a spatial resolution exceeding the predetermined optic resolution,
repeating the foregoing steps several times, and a plurality of individual images resulting therefrom being combined to an overall image, using at least one of the following:
a cylindrical lens as an anamorphotic optic in an imaging beam path the orientation and shape of displayed particles or molecules determining their vertical (Z) position,
splitting into at least two partial detection radiation paths in the detection radiation path with different optic lengths, detected off-set on the detector;
point-scanning or line scanning for activation or switching.

11. The method according to claim 10, wherein said spectral splitting element is a grid.

12. The high-resolution microscope according to claim 1, further comprising means for selective activation or switching sample regions, and a grid provided which spectrally splits laser pulses for activation or switching.

13. The high-resolution microscope according to claim 12, wherein said split radiation portions being combined in the image level or in the sample in a telescopic radiation path.

14. The high-resolution microscope according to claim 13, wherein wide-field irradiation and detection are provided for exciting said sample.

15. The high-resolution microscope according to claim 12, further comprising a spatially resolving sensor provided for line detection, and a slit diaphragm being opened such that at least two rows of sensors, each comprising several sensors, are radiated with sample light.

16. The high-resolution microscope according to claim 12, further comprising a micro-lens array provided for multiphoton switching or activation.

17. The high-resolution microscope according to claim 12, wherein said means for a selective activation or switching is an acousto-optical tunable filter (AOTF).

18. The high-resolution microscope according to claim 12, wherein said means for a selective activation or switching is a spatial light modulator (SLM) arranged downstream in reference to said grid in the radiation path for the selection of spectrally split laser pulse portions.

19. The high-resolution microscope according to claim 12, wherein said means for a selective activation or switching is digital micro-mirror device (DMD) arranged downstream in reference to said grid in the radiation path for the selection of spectrally split laser pulse portions.

20. The method according to claim 10, further comprising activating or switching sample regions manually or automatically.

21. The method according to claim 10, wherein said activating or switching is by multiphoton excitation.

22. The method according to claim 10, wherein said split radiation portions being combined in the image level or in the sample in a telescopic radiation path.

23. The method according to claim 10, wherein said excitation of said sample and detection of said sample light occurring in the wide-field.

24. The method according to claim 10, further comprising a spatially resolving sensor provided for line detection, and a slit diaphragm being opened such that at least two rows of sensors, each comprising several sensors, are radiated with sample light.

25. The method according to claim 10, further comprising a micro-lens array provided for multiphoton switching or activation, said sensors being provided side-by-side in a 45 degree arrangement.

26. The method according to claim 10, wherein said activating or switching occurs by acousto-optical tunable filter (AOTF).

27. The method according to claim 10, wherein said activating or switching occurs by spatial light modulation (SLM).

28. The method according to claim 10, wherein said activating or switching occurs by a digital micro-mirror device (DMD).

29. The method according to claim 10, further comprising using a spectral splitting element, laser pulses being spectrally split for activation or switching.

30. The method according to claim 11, further comprising a SLM or DMD for controlled selection of split laser pulse portions in the radiation path downstream in reference to the grid.

31. The method according to claim 23, the laser wide-field excitation is guided by SLM or DMD.

32. The method according to claim 10, wherein regions of interest in said sample being selected by SLM or DMD.

33. The method according to claim 21, wherein multiphoton switching or activating occurs via a micro-lens array.

34. The method according to claim 10, wherein switching or activating occurs via a line scanner.

35. The method according to claim 10, wherein a line detection occurs via a spatially resolving sensor, with irradiation occurring via a slit diaphragm setting with at least two rows of sensors, each comprising several sensors.

36. The method according to claim 21, wherein said multiphoton excitation process is two-photon excitation.

37. The method according to claim 25, wherein said micro-lens array is a cylinder lens array.

38. The microscope according to claim 21, further comprising a micro-lens array for multiphoton switching or activation, said micro-lens array is a cylinder lens array.

39. The high-resolution microscope according to claim 12, wherein said non-linear excitation is two photon excitation.

40. The high-resolution microscope according to claim 16, wherein said sensors are provided side-by-side in a 45 degree arrangement.

* * * * *